(12) United States Patent
Okamura et al.

(10) Patent No.: US 12,338,282 B2
(45) Date of Patent: *Jun. 24, 2025

(54) ANTI-NOTCH3 ANTIBODY

(71) Applicant: AVEO Pharmaceuticals, Inc., Boston, MA (US)

(72) Inventors: Heidi Okamura, Brookline, MA (US); William M. Winston, Jr., Marlborough, MA (US); Laura Poling, Boston, MA (US); Alisa C. Bell, Bedford, MA (US)

(73) Assignee: AVEO Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/450,282

(22) Filed: Oct. 7, 2021

(65) Prior Publication Data

US 2022/0235127 A1 Jul. 28, 2022

Related U.S. Application Data

(63) Continuation of application No. 16/097,489, filed as application No. PCT/US2017/030156 on Apr. 28, 2017, now Pat. No. 11,142,573.

(60) Provisional application No. 62/460,371, filed on Feb. 17, 2017, provisional application No. 62/329,729, filed on Apr. 29, 2016.

(51) Int. Cl.
| | |
|---|---|
| A61K 39/395 | (2006.01) |
| A61P 35/00 | (2006.01) |
| C07K 16/28 | (2006.01) |
| C07K 16/30 | (2006.01) |
| C12N 5/10 | (2006.01) |
| C12N 5/12 | (2006.01) |
| C12N 15/63 | (2006.01) |
| A61K 39/00 | (2006.01) |
| C07K 14/71 | (2006.01) |

(52) U.S. Cl.
CPC .......... *C07K 16/28* (2013.01); *A61K 39/3955* (2013.01); *A61K 39/39558* (2013.01); *A61P 35/00* (2018.01); *C07K 16/2863* (2013.01); *C07K 16/30* (2013.01); *C12N 5/10* (2013.01); *C12N 5/12* (2013.01); *C12N 15/63* (2013.01); *A61K 2039/505* (2013.01); *C07K 14/71* (2013.01); *C07K 2317/21* (2013.01); *C07K 2317/33* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search
CPC ........ A61K 2039/505; A61K 39/39558; A61K 39/3955; A61K 39/395; A61K 39/00; A61K 39/39533; C07K 16/28; C07K 2317/56; C07K 2317/76; C07K 2317/565; C07K 2317/92; C07K 16/30; C07K 2317/24; C07K 16/2863; C07K 16/18; C07K 14/705; C07K 2317/73; C07K 16/2896; C07K 2317/734; C07K 14/71

See application file for complete search history.

(56) References Cited

U.S. PATENT DOCUMENTS

| | | | |
|---|---|---|---|
| 6,399,857 B1 | 6/2002 | Kloti | |
| 7,544,476 B1 | 6/2009 | O'Hagan et al. | |
| 7,915,390 B2 * | 3/2011 | Li | C07K 16/30 530/387.9 |
| 7,935,791 B2 * | 5/2011 | Fung | A61P 35/00 530/387.9 |
| 7,994,285 B2 * | 8/2011 | Li | C07K 16/00 530/387.3 |
| 8,425,903 B2 | 4/2013 | Gurney et al. | |
| 9,200,071 B2 * | 12/2015 | Siebel | A61P 35/02 |
| 9,879,083 B2 * | 1/2018 | Okamura | C12N 15/63 |
| 10,745,476 B2 * | 8/2020 | Okamura | C07K 16/28 |
| 11,142,573 B2 * | 10/2021 | Okamura | C12N 5/10 |
| 2010/0111958 A1 | 5/2010 | Gurney et al. | |
| 2013/0323266 A1 * | 12/2013 | Hoey | A61P 35/00 424/172.1 |
| 2014/0127211 A1 * | 5/2014 | Geles | C07K 16/3046 530/331 |
| 2017/0023576 A1 * | 1/2017 | Cancilla | A61K 39/39558 |

FOREIGN PATENT DOCUMENTS

| | | |
|---|---|---|
| WO | WO-2008091641 A2 | 7/2008 |
| WO | WO-2010005566 A2 | 1/2010 |
| WO | WO-2011041336 A2 | 4/2011 |
| WO | WO-2012003472 A1 | 1/2012 |
| WO | WO-2014100435 A1 | 6/2014 |
| WO | WO-2014159239 A2 | 10/2014 |
| WO | WO-2016046053 A1 * | 3/2016 |

OTHER PUBLICATIONS

Aburjania et al. The role of Notch3 in cancer. The Oncologist 23: 900-911, 2018.*
Bellavia et al. Notch3: from subtle structural differences to functional divesity. Oncogene 27: 5092-5098, 2008.*
Cui et al. Notch3 functions as a tumor suppressor by controlling cellular senescence. Cancer Res 73(11): 3451-3459, 2013.*
Hosseini-Alghaderi et al. Notch3 in development, health and disease. Biomolecules 10: 485, 2020 (17 total pages).*
Inder et al. The Notch-3 receptor: a molecular switch to tumorigenesis? Cancer Treat Rev 60: 69-76, 2017.*

(Continued)

Primary Examiner — Bridget E Bunner
(74) Attorney, Agent, or Firm — Dechert LLP

(57) ABSTRACT

Monoclonal antibodies that bind and inhibit activation of human Notch3 are disclosed. The antibodies can be used to treat cell proliferative diseases and disorders, including certain forms of cancer, associated with activation and/or overexpression of Notch3.

13 Claims, 16 Drawing Sheets

Specification includes a Sequence Listing.

(56) References Cited

OTHER PUBLICATIONS

Rusanescu et al. Notch signaling in cardiovascular disease and calcification. Curr Cardiol Rev 4: 148-156, 2008.*
Song et al. Cancer stem cells—an old idea that's new again: implications for the diagnosis and treatment of brease cancer. Expert Opin Biol Ther 7(4): 431-438, 2007.*
Tannock and Hill. The Basic Science of Oncology. 1998. New York: McGraw-Hill;; pp. 357-358.*
Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993 (abstract).*
Burks et al. In vitro scanning saturation mutagenesis of an antibody binding pocket. Proc Natl Acad Sci USA 94: 412-417, 1997.*
Cassett et al. A peptide mimetic of an anti-CD4 monoclonal antibody by rationale design. Biochem Biophys Res Comm 307: 198-205, 2003.*
Chen et al. J Mol Biol 293: 865-881, 1999.*
Colman Research in Immunol. 145:33-36, 1994.*
De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.*
Holm et al. Functional mapping and single chain construction of the anti-cytokeratin 8 monoclonal antibody TS1. Mol Immunol 44: 1075-1084, 2007.*
Jang et al. The structural basis for DNA binding by an anti-DNA autobody. Mol Immunol 35: 1207-1217, 1998.*
Kobayashi et al. Tryptophan H33 plays an important role in pyrimidine (6-4) pyrimidone photoproduct binding by a high-affinity antibody. Protein Engineering 12(10): 879-884, 1999.*
MacCallum et al. Antibody-antigen interactions: contact analysis and binding site topography. J Mol Biol 262: 732-745, 1996.*
Paul, William E., Fundamental Immunology, 3rd Edition, Raven Press, New York, Chapt. 8, pp. 292-295 (1993).*
Raimondi et al. Inhibition of Notch3 signalling induces rhabdomyosarcoma cell differentiation promoting p38 phosphorylation and p21Cip1 expresson and hampers tumour cell growth in vitro and in vivo. Cell Death Differentiation 19: 871-881, 2012.*
Rudikoff et al. Single amino acid substitution altering antigen-binding specificity. Proc Natl Acad Sci USA 79: 1979-1983, 1982.*
Sela-Culang et al. The structural basis of antibody-antigen recognition. Front Immunol 4: 302, 2013 (13 total pages).*
Vajdos et al. Comprehensive functional maps of the antigen-binding site of an anti-ErbB2 antibody obtained with shotgun scanning mutagenesis. J Mol Biol 320: 415-428, 2002.*
Van Nes et al. A Notch3 transcriptional module induces cell motility in neuroblastoma. Clin Cancer Res 19(13): 3485-3494, 2013.*
Vasudevan et al. A single amino acid change in the binding pocket alters specificity of an anti-integrin antibody AP7.4 as revealed by its crystal structure. Blood Cell Mol Dis 32: 176-181, 2004.*
Wu et al. Humanization of a murine monoclonal antibody by simultaneous optimization of framework and CDR residues. J Mol Biol 294: 151-162, 1999.*
Zhang et al. Comprehensive optimization of a single-chain variable domain antibody fragment as a targeting ligand for a cytotoxic nanoparticle. mAbs 7(1): 42-52, 2015.*
Aste-Amezaga et al., "Characterization of Notch1 Antibodies that Inhibit Signaling of Both Normal and Mutated Notch1 Receptors," PLoS One. 2010;5(2):e9094.
Bellavia et al., "Combined expression of pTalpha and Notch3 in T cell leukemia identifies the requirement of preTCR for leukemogenesis," Proc Natl Acad Sci USA. 2002;99(6):3788-93.
Bellavia et al., "Constitutive activation of NF-kappaB and T-cell leukemia/lymphoma in Notch3 transgenic mice," EMBO. 2000;19(13):3337-48.
Bray, "Notch Signalling: A Simple Pathway Becomes Complex," Nat Rev Mol Cell Biol. 2006;7(9):678-89.
Falk et al., "Generation of anti-Notch antibodies and their application in blocking Notch signalling in neural stem cells," Methods, 2012;58(1):69-78.
Haruki et al., "Dominant-negative Notch3 receptor inhibits mitogen-activated protein kinase pathway and the growth of human lung cancers," Cancer Res. 2005;65(9):3555-61.
Jaye et al., "Isolation of a human anti-haemophilic factor IX cDNA clone using a unique 52-base synthetic oligonucleotide probe deduced from the amino acid sequence of bovine factor IX," Nucleic Acids Res. 1983;11(8):2325-35.
Joutel et. al., "Skin biopsy immunostaining with a Notch3 monoclonal antibody for CADASIL diagnosis," Lancet. 2001;358(9298):2049-51.
Kopan and Ilagan, "The Canonical Notch Signaling Pathway: Unfolding the Activation Mechanism," Cell. 2009;137(2):216-33.
Lewin, "Genes IV," Cell Press. 1990;Ch. 7:118-120.
Li et al., "Modulation of Notch signaling by antibodies specific for the extracellular negative regulatory region of NOTCH3," J. Biol. Chem. 2008;283(12):8046-54.
Lin et al., "Targeting specific regions of the Notch3 ligand-binding domain induces apoptosis and inhibits tumor growth in lung cancer," Cancer Res. 2010;70(2):632-8.
Lloyd et al., "Modelling the human immune response: performance of a 1011 human antibody repertoire against a broad panel of therapeutically relevant antigens," Protein Eng Des Sel. 2009;22(3):159-68.
Miele et al., "NOTCH Signaling as a Novel Cancer Therapeutic Target," Curr Cancer Drug Targets. 2006;6(4):313-23.
Park et al., "Notch3 gene amplification in ovarian cancer," Cancer Res. 2006;66(12):6312-8.
PCT International Search Report and Written Opinion from PCT/US2017/030156, dated Sep. 8, 2017.
Sambrook et al., "Molecular Cloning a Labratory Manual," 2nd Edition, Cold Spring Harbor, N.Y., 1989;2.43-2.84.
Sansone et al., "IL-6 triggers malignant features in mammospheres from human ductal breast carcinoma and normal mammary gland," J. Clin Invest. 2007;117(12):3988-4002.
Tiyanont et al., "Insights into Notch3 activation and inhibition mediated by antibodies directed against its negative regulatory region," J. Mol. Biol. 2013;425(17):3192-204.
Wu et al., "Therapeutic Antibody Targeting of Individual Notch Receptors," Nature. 2010;464(7291):1052-7.

* cited by examiner

FIG. 2A

Human Notch3 ECD (amino acids 40-1643)

```
                                          40         50         60
                                       A PPCLDGSPCA NGGRCTQLPS 70         80         90        100        110        120
REAACLCPPG WVGERCQLED PCHSGPCAGR GVCQSSVVAG TARFSCRCPR GFRGPDCSLP 130        140        150        160        170        180
DPCLSSPCAH GARCSVGPDG RFLCSCPPGY QGRSCRSDVD ECRVGEPCRH GGTCLNTPGS 190        200        210        220        230        240
FRCQCPAGYT GPLCENPAVP CAPSPCRNGG TCRQSGDLTY DCACLPGFEG QNCEVNVDDC 250        260        270        280        290        300
PGHRCLNGGT CVDGVNTYNC QCPPEWTGQF CTEDVDECQL QPNACHNGGT CFNTLGGHSC 310        320        330        340        350        360
VCVNGWTGES CSQNIDDCAT AVCFHGATCH DRVASFYCAC PMGKTGLLCH LDDACVSNPC 370        380        390        400        410        420
HEDAICDTNP VNGRAICTCP PGFTGGACDQ DVDECSIGAN PCEHLGRCVN TQGSFLCQCG 430        440        450        460        470        480
RGYTGPRCET DVNECLSGPC RNQATCLDRI GQFTCICMAG FTGTYCEVDI DECQSSPCVN 490        500        510        520        530        540
GGVCKDRVNG FSCTCPSGFS GSTCQLDVDE CASTPCRNGA KCVDQPDGYE CRCAEGFEGT 550        560        570        580        590        600
LCDRNVDDCS PDPCHHGRCV DGIASFSCAC APGYTGTRCE SQVDECRSQP CRHGGKCLDL 610        620        630        640        650        660
VDKYLCRCPS GTTGVNCEVN IDDCASNPCT FGVCRDGINR YDCVCQPGFT GPLCNVEINE
```

CASSPCGEGG SCVDGENGFR CLCPPGSLPP LCLPPSHPCA HEPCSHGICY DAPGGFRCVC 730        740        750        760        770        780

EPGWSGPRCS QSLARDACES QPCRAGGTCS SDGMGFHCTC PPGVQGRQCE LLSPCTPNPC 790        800        810        820        830        840

EHGGRCESAP GQLPVCSCPQ GWQGPRCQQD VDECAGPAPC GPHGICTNLA GSFSCTCHGG 850        860        870        880        890        900

YTGPSCDQDI NDCDPNPCLN GGSCQDGVGS FSCSCLPGFA GPRCARDVDE CLSNPCGPGT 910        920        930        940        950        960

CTDHVASFTC TCPPGYGGFH CEQDLPDCSP SSCFNGGTCV DGVNSFSCLC RPGYTGAHCQ 970        980        990       1000       1010       1020

HEADPCLSRP CLHGGVCSAA HPGFRCTCLE SFTGPQCQTL VDWCSRQPCQ NGGRCVQTGA 1030       1040       1050       1060       1070       1080

YCLCPPGWSG RLCDIRSLPC REAAAQIGVR LEQLCQAGGQ CVDEDSSHYC VCPEGRTGSH 1090       1100       1110       1120       1130       1140

CEQEVDPCLA QPCQHGGTCR GYMGGYMCEC LPGYNGDNCE DDVDECASQP CQHGGSCIDL 1150       1160       1170       1180       1190       1200

VARYLCSCPP GTLGVLCEIN EDDCGPGPPL DSGPRCLHNG TCVDLVGGFR CTCPPGYTGL 1210       1220       1230       1240       1250       1260

RCEADINECR SGACHAAHTR DCLQDFGGGF RCLCHAGFSG PRCQTVLSPC ESQPCQHGGQ 1270       1280       1290       1300       1310       1320

CRPSPGPGGG LTFTCHCAQP FWGPRCERVA RSCRELQCPV GVPCQQTPRG PRCACPPGLS 1330       1340       1350       1360       1370       1380

GPSCRSFPGS PPGASNASCA AAPCLHGGSC RPAPLAPFFR CACAQGWTGP RCEAPAAAPE 1390       1400       1410       1420       1430       1440
```

FIG. 2C

```
VSEEPRCPRA ACQAKRGDQR CDRECNSPGC GWDGGDCSLS VGDPWRQCEA LQCWRLFNNS
    1450       1460       1470       1480       1490       1500

RCDPACSSPA CLYDNFDCHA GGRERTCNPV YEKYCADHFA DGRCDQGCNT EECGWDGLDC
    1510       1520       1530       1540       1550       1560

ASEVPALLAR GVLVLTVLLP PEELLRSSAD FLQRLSAILR TSLRFRLDAH GQAMVFPYHR
    1570       1580       1590       1600       1610       1620

PSPGSEPRAR RELAPEVIGS VVMLEIDNRL CLQSPENDHC FPDAQSAADY LGALSAVERL
    1630       1640

DFPYPLRDVR GEPLEPPEPS VPL   (SEQ ID NO:19)
```

FIG. 3

Human Notch3 EGF-Like Repeats 1-11 (amino acids 40-467)

```
                                         40         50         60
                                     A PPCLDGSPCA NGGRCTQLPS 70         80         90        100        110        120
REAACLCPPG WVGERCQLED PCHSGPCAGR GVCQSSVVAG TARFSCRCPR GFRGPDCSLP 130        140        150        160        170        180
DPCLSSPCAH GARCSVGPDG RFLCSCPPGY QGRSCRSDVD ECRVGEPCRH GGTCLNTPGS 190        200        210        220        230        240
FRCQCPAGYT GPLCENPAVP CAPSPCRNGG TCRQSGDLTY DCACLPGFEG QNCEVNVDDC 250        260        270        280        290        300
PGHRCLNGGT CVDGVNTYNC QCPPEWTGQF CTEDVDECQL QPNACHNGGT CFNTLGGHSC 310        320        330        340        350        360
VCVNGWTGES CSQNIDDCAT AVCFHGATCH DRVASFYCAC PMGKTGLLCH LDDACVSNPC 370        380        390        400        410        420
HEDAICDTNP VNGRAICTCP PGFTGGACDQ DVDECSIGAN PCEHLGRCVN TQGSFLCQCG 430        440        450        460
RGYTGPRCET DVNECLSGPC RNQATCLDRI GQFTCICMAG FTGTYCE (SEQ ID NO: 20)
```

FIG. 4 evqllesggglvqpggslrlscaasgftfs|dymms|wvrqapgkglewv
                               CDR<sub>H1</sub> s|wirssggttlyadsvkg|rftisrdnskntlylqmnslraedtatyyc
  CDR<sub>H2</sub> ar|vgggttgyafdi|wgqgtmvtvss (SEQ ID NO: 6)
   CDR<sub>H3</sub>

Heavy Chain Variable Region of Antibody 28042

FIG. 5 diqmtqspsslsasvgdrvtitc|rasqsisnyln|wyqqkpgka
                       CDR_L1 pklliy|gasslqs|gvpsrvsgtgsgtdftltisslqpedfaty
       CDR_L2 yc|qqsyspsft|fgpgtkvdfe   (SEQ ID NO:10)
   CDR_L3

Kappa Chain Variable Region of Antibody 28042

Notch3 ICD Cleavage Assay in NCI-H838

```
28042                      diqmtqspssisasvgdrvtitcrasqsisnylnwyqqkpgkapklliygasslqs
28042.1  N31S              diqmtqspssisasvgdrvtitcrasqsisSylnwyqqkpgkapklliygasslqs
28042.2  G50A              diqmtqspssisasvgdrvtitcrasqsisnylnwyqqkpgkapklliyAasslqs
28042.3  F106I             diqmtqspssisasvgdrvtitcrasqsisnylnwyqqkpgkapklliygasslqs
28042.4  E107K             diqmtqspssisasvgdrvtitcrasqsisnylnwyqqkpgkapklliygasslqs
28042.5  N31S, G50A        diqmtqspssisasvgdrvtitcrasqsisSylnwyqqkpgkapklliyAasslqs
28042.6  F106I, E107K      diqmtqspssisasvgdrvtitcrasqsisnylnwyqqkpgkapklliygasslqs
28042.7  N31S, G50A,       diqmtqspssisasvgdrvtitcrasqsisSylnwyqqkpgkapklliyAasslqs
         F106I, E107K
28042.8  V62F              diqmtqspssisasvgdrvtitcrasqsisnylnwyqqkpgkapklliygasslqs
28042.9  T65S              diqmtqspssisasvgdrvtitcrasqsisnylnwyqqkpgkapklliygasslqs
28042.10 N31S, G50A,       diqmtqspssisasvgdrvtitcrasqsisSylnwyqqkpgkapklliyAasslqs
         V62F, T65S
                                                  CDR_L1

28042                      gvpsrvsgtgsgtdftltisslqpedfatyycqqsyspsftfgpgtkvdfe   (SEQ ID NO:10)
28042.1  N31S              gvpsrvsgtgsgtdftltisslqpedfatyycqqsyspsftfgpgtkvdfe   (SEQ ID NO:23)
28042.2  G50A              gvpsrvsgtgsgtdftltisslqpedfatyycqqsyspsftfgpgtkvdfe   (SEQ ID NO:24)
28042.3  F106I             gvpsrvsgtgsgtdftltisslqpedfatyycqqsyspsftIgpgtkvdfe   (SEQ ID NO:25)
28042.4  E107K             gvpsrvsgtgsgtdftltisslqpedfatyycqqsyspsftfgpgtkvdIK   (SEQ ID NO:26)
28042.5  N31S, G50A        gvpsrvsgtgsgtdftltisslqpedfatyycqqsyspsftfgpgtkvdfe   (SEQ ID NO:27)
28042.6  F106I, E107K      gvpsrvsgtgsgtdftltisslqpedfatyycqqsyspsftIgpgtkvdIK   (SEQ ID NO:28)
28042.7  N31S, G50A,       gvpsrvsgtgsgtdftltisslqpedfatyycqqsyspsftIgpgtkvdIK   (SEQ ID NO:29)
         F106I, E107K
28042.8  V62F              gvpsrvsgtgsgtdftltisslqpedfatyycqqsyspsftfgpgtkvdfe   (SEQ ID NO:37)
28042.9  T65S              gvpsrvsgSgsgtdftltisslqpedfatyycqqsyspsftfgpgtkvdfe   (SEQ ID NO:38)
28042.10 N31S, G50A,       gvpsrFsgSgsgtdftltisslqpedfatyycqqsyspsftfgpgtkvdfe   (SEQ ID NO:39)
         V62F, T65S
                                                  CDR_L3
```

Complete Light (Kappa) Chain Variable Region Amino Acid Sequence Alignments

FIG. 13

| | | |
|---|---|---|
| 28042 | rasqsisnyln (SEQ ID NO:7) | gasslqs (SEQ ID NO:8) |
| 28042.1 N31S | rasqsisSyln (SEQ ID NO:21) | gasslqs (SEQ ID NO:8) |
| 28042.2 G50A | rasqsisnyln (SEQ ID NO:7) | Aasslqs (SEQ ID NO:22) |
| 28042.3 F106I | rasqsisnyln (SEQ ID NO:7) | gasslqs (SEQ ID NO:8) |
| 28042.4 E107K | rasqsisnyln (SEQ ID NO:7) | gasslqs (SEQ ID NO:8) |
| 28042.5 N31S, G50A | rasqsisSyln (SEQ ID NO:21) | Aasslqs (SEQ ID NO:22) |
| 28042.6 F106I, E107K | rasqsisnyln (SEQ ID NO:7) | gasslqs (SEQ ID NO:8) |
| 28042.7 N31S, G50A, F106I, E107K | rasqsisSyln (SEQ ID NO:21) | Aasslqs (SEQ ID NO:22) |
| 28042.8 V62F | rasqsisnyln (SEQ ID NO:7) | gasslqs (SEQ ID NO:8) |
| 28042.9 T65S | rasqsisnyln (SEQ ID NO:7) | gasslqs (SEQ ID NO:8) |
| 28042.10 N31S, G50A, V62F, T65S | rasqsisSyln (SEQ ID NO:21) | Aasslqs (SEQ ID NO:22) |
| | CDR$_{L1}$ | CDR$_{L2}$ |

| | |
|---|---|
| 28042 | qqsyspsft (SEQ ID NO:9) |
| 28042.1 N31S | qqsyspsft (SEQ ID NO:9) |
| 28042.2 G50A | qqsyspsft (SEQ ID NO:9) |
| 28042.3 F106I | qqsyspsft (SEQ ID NO:9) |
| 28042.4 E107K | qqsyspsft (SEQ ID NO:9) |
| 28042.5 N31S, G50A | qqsyspsft (SEQ ID NO:9) |
| 28042.6 F106I, E107K | qqsyspsft (SEQ ID NO:9) |
| 28042.7 N31S, G50A, F106I, E107K | qqsyspsft (SEQ ID NO:9) |
| 28042.8 V62F | qqsyspsft (SEQ ID NO:9) |
| 28042.9 T65S | qqsyspsft (SEQ ID NO:9) |
| 28042.10 N31S, G50A, V62F, T65S | qqsyspsft (SEQ ID NO:9) |
| | CDR$_{L3}$ |

Light (Kappa) Chain CDR Amino Acid Alignments

FIG. 14

ANTI-NOTCH3 ANTIBODY

CROSS-REFERENCE TO RELATED APPLICATIONS

This application is a continuation of U.S. patent application Ser. No. 16/097,489 filed Oct. 29, 2018, which is a U.S. national stage application under 35 U.S.C. § 371 of International Application No. PCT/US2017/030156 filed Apr. 28, 2017, which claims the benefit of and priority to U.S. Provisional Patent Application No. 62/460,371 filed Feb. 17, 2017, and U.S. Provisional Application No. 62/329,729, filed Apr. 29, 2016, the contents of each of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Oct. 7, 2021, is named AVO-040C1-SL.txt and is 65,366 bytes in size.

FIELD OF THE INVENTION

The field of the invention is molecular biology, specifically immunology and antibodies that bind human Notch3.

BACKGROUND

Notch pathway signaling is involved in numerous cellular processes, including cell fate determination, differentiation, proliferation, apoptosis, migration and angiogenesis. In mammals, there are four Notch proteins (sometimes called "Notch receptors"), designated Notch1-Notch4. All four Notch proteins have a similar domain structure, which includes an extracellular domain, a negative regulatory (NRR) domain, a single-pass transmembrane domain, and an intracellular domain. The extracellular domain contains a series of EGF-like repeats that are involved in ligand binding. During maturation, the Notch polypeptide is cleaved by a furin-like protease. This cleavage divides the Notch protein into two subunits that are held together by the NRR. In the absence of ligand binding, the NRR domain functions to keep the Notch protein in a protease-resistant conformation. The intracellular domain is a transcription factor called Notch intracellular domain (NICD), which is released upon proteolytic cleavage by gamma secretase, in response to binding of the Notch protein by a ligand. In mammals, the Notch ligands are Delta-like (e.g., DLL1 and DLL4) and Jagged (also referred to as Jag, e.g., Jag1 and Jag2). When the NICD is released, it travels to the nucleus, where it activates transcription of the Notch-responsive genes, HES1, HES5, NRARP, Deltex1 and c-MYC. For reviews of Notch-related biology, see, e.g., Bray, 2006, NATURE REVIEWS 7:678-689; Kopan et al., 2009, CELL 137:216-233.

While Notch proteins play crucial roles in normal development, dysregulation of the Notch proteins is associated with various types of cancer, including T-cell acute lymphatic leukemia/lymphoma (T-All), breast cancer, colon cancer, ovarian cancer and lung cancer. See, e.g., Miele et al., 2006, CURRENT CANCER DRUG TARGETS 6:313-323. Accordingly, one therapeutic approach for the treatment of cancer is inhibition of Notch pathway signaling. Inhibition of Notch pathway signaling has been achieved using monoclonal antibodies (Wu et al., 2010, NATURE 464: 1052-1057; Aste-Amézaga et al., 2010, PLOS ONE 5:1-13 e9094). Further, dysregulation of Notch may be associated with development of pulmonary arterial hypertension (PAH). Accordingly, a therapeutic approach to treating PAH may involve inhibition of the Notch pathway signaling. (Li et al., 2009, Nature Medicine, 15:1289-1299; Jalali et al., 2012, PLOS ONE 7:e46808; Yu et al., 2013, Am. J. Respir. Cell Mol. Biol., 48:647-654; Chida et al., 2014, Mol Gen. & Gen. Med., 2:229-239.)

Naturally-occurring antibodies are multimeric proteins that contain four polypeptide chains (FIG. 1). Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($CH_1$, $CH_2$ and $CH_3$ in FIG. 1). The variable regions determine the specificity of the antibody.

Each variable region contains three hypervariable regions known as complementarity determining regions (CDRs) flanked by four relatively conserved regions known as framework regions (FRs). The three CDRs, referred to as $CDR_1$, $CDR_2$, and $CDR_3$, contribute to the antibody binding specificity. Naturally occurring antibodies have been used as starting material for engineered antibodies, such as chimeric antibodies and humanized antibodies.

There is a need for improved antibodies that neutralize the biological activity of human Notch3 and that can be used as therapeutic agents to treat human patients.

SUMMARY OF THE INVENTION

The invention is based, in part, upon the discovery of antibodies that specifically bind human Notch3. Antibodies disclosed herein contain human Notch3 binding sites based on the CDRs of the anti-Notch3 antibodies described herein. The antibodies can be used as therapeutic agents, and, depending upon the intended uses, can be optimized, e.g., affinity-matured, to improve biochemical properties (e.g., affinity and/or specificity), to improve biophysical properties (e.g., aggregation, stability, precipitation, and/or non-specific interactions), and/or to reduce or eliminate immunogenicity, when administered to a human subject.

The disclosed antibodies prevent or inhibit activation of human Notch3, which they do by inhibiting Notch3 from binding to Notch ligands, i.e., Jag1, Jag2, DLL1, and DLL4. The disclosed antibodies can be used to inhibit the proliferation of tumor cells in vitro and/or in vivo. When administered to a human subject with cancer, the antibodies inhibit or reduce tumor growth in the subject. When administered to a human with pulmonary arterial hypertension (PAH), the antibodies treat, reduce, or alleviate the symptoms and/or causes of PAH.

These and other aspects and advantages of the invention are illustrated by the following figures, detailed description and claims.

DESCRIPTION OF THE DRAWINGS

The invention can be more completely understood with reference to the following drawings.

FIGS. 2A-C provides the amino acid sequence corresponding to the extracellular domain (ECD; amino acids 40 to 1643) of human Notch3 (SEQ ID NO:19).

FIG. 3 provides the amino acid sequence corresponding to EGF-like repeats 1-11 (amino acids 40 to 467 of the extracellular domain shown in FIG. 2) of human Notch3 (SEQ ID NO:20).

FIG. 4 shows the amino acid sequence for the complete heavy chain variable region (SEQ ID NO:6) of antibody 28042. Sequences corresponding to $CDR_1$ (SEQ ID NO:3), $CDR_2$ (SEQ ID NO:4), and $CDR_3$ (SEQ ID NO:5) are identified in boxes. The unboxed sequences represent framework (FR) sequences.

FIG. 5 shows the amino acid sequence for the complete light (kappa) chain variable region (SEQ ID NO:10) of antibody 28042. Sequences corresponding to $CDR_1$ (SEQ ID NO:7), $CDR_2$ (SEQ ID NO:8), and $CDR_3$ (SEQ ID NO:9) are identified in boxes. The unboxed sequences represent framework (FR) sequences.

FIG. 10A is a Western blot that shows the level of inhibition of Jag1, Jag2, and DLL4 induced Notch3 activation by the 28042 antibody as assessed by extent of intracellular domain cleavage of murine Notch3 expressed in FlpIn™ cells. FIG. 10B is a Western blot that shows the level of inhibition of Jag1, Jag2, and DLL4 induced Notch3 activation by the 28042 antibody as assessed by extent of intracellular domain cleavage of human Notch3 expressed in FlpIn™ cells.

FIG. 12A shows the tumor volume over time (in days) for mice treated with hIgG or the 28042 antibody. The 28042 antibody showed significant tumor growth inhibition compared to the IgG control. FIG. 12B depicts results of Western blotting performed on lysate of harvested tumors using an antibody specific for the Notch3 C-terminus in order to detect the extent of Notch intracellular domain cleavage. β-tubulin was used as a loading control.

FIG. 13 shows an alignment of the light chain variable region amino acid sequences for the 28042 antibody and variants 28042.1-28042.10. CDRs are identified by bold lettering and boxes.

FIG. 14 shows the light chain CDRs for the 28042 antibody and variants 28042.1-28042.10.

DETAILED DESCRIPTION

Figure 1:
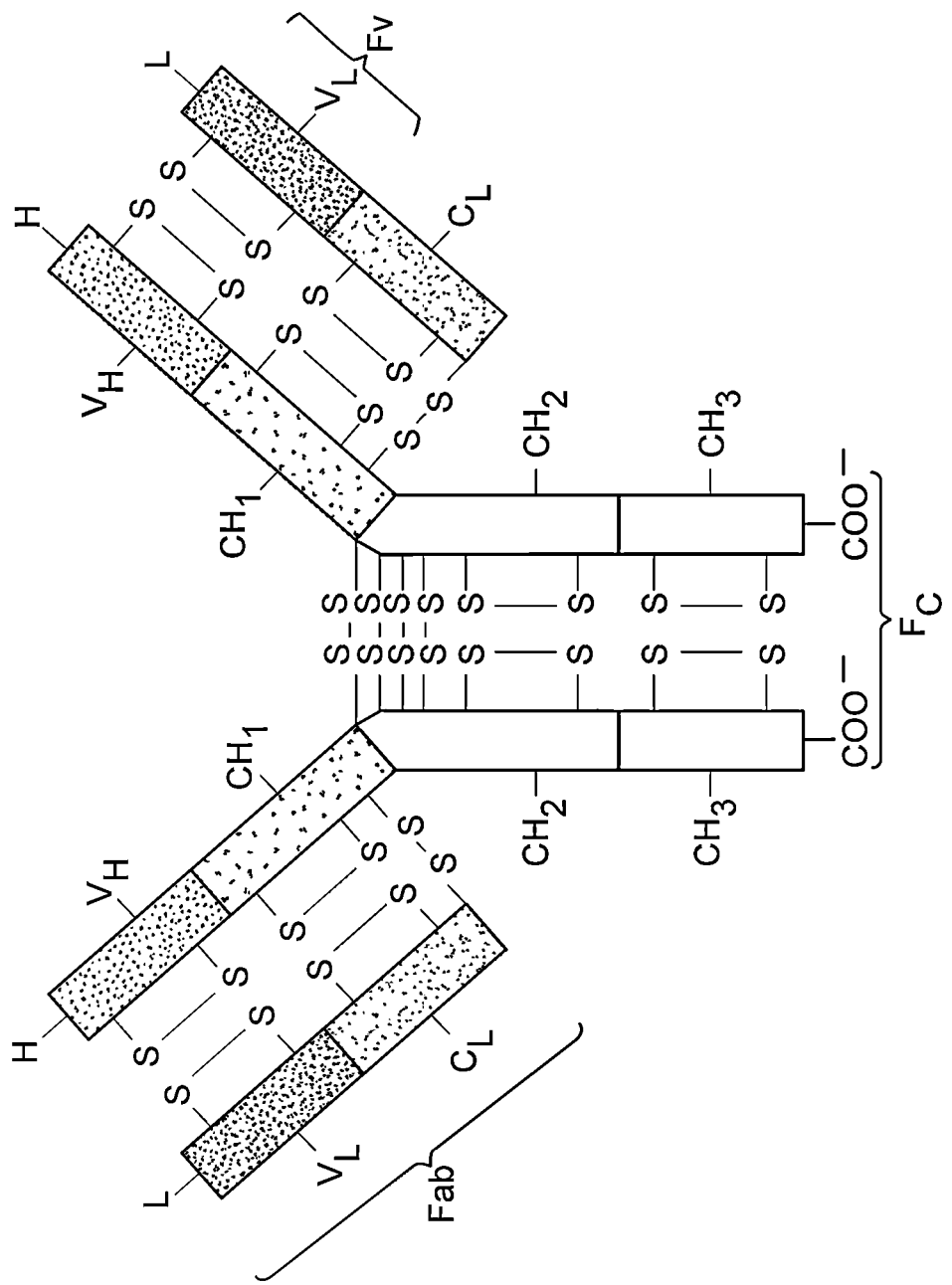
FIG. 1 is a schematic representation of a typical, naturally-occurring antibody.

The antibodies disclosed herein are based on the antigen binding sites of certain monoclonal antibodies that have been selected on the basis of binding and neutralizing the activity of human Notch3. The antibodies contain immunoglobulin variable region CDR sequences that define a binding site for human Notch3.

Because of the neutralizing activity of these antibodies, they can be used to inhibit the growth and/or proliferation of certain cancer cells and tumors and for treating pulmonary arterial hypertension (PAH) or other conditions where the Notch3 pathway is involved. When used as a therapeutic agent, the antibodies can be optimized, e.g., affinity-matured, to improve biochemical properties and/or biophysical properties, and/or to reduce or eliminate immunogenicity when administered to a human patient. Various features and aspects of the invention are discussed in more detail below.

As used herein, unless otherwise indicated, the term "antibody" means an intact antibody (e.g., an intact monoclonal antibody) or antigen-binding fragment of an antibody, including an intact antibody or antigen-binding fragment that has been modified, engineered or chemically conjugated. Examples of antibodies that have been modified or engineered are chimeric antibodies, humanized antibodies, and multispecific antibodies (e.g., bispecific antibodies). Examples of antigen-binding fragments include Fab, Fab', $F(ab')_2$, Fv, single chain antibodies (e.g., scFv), minibodies, and diabodies. An antibody conjugated to a toxin moiety is an example of a chemically conjugated antibody.

I. Antibodies that Bind Human Notch3

As disclosed herein, the antibodies may comprise: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding human Notch3.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region, wherein the heavy chain variable region and the light chain variable region together define a single binding site for binding hNotch3. A $CDR_{H1}$ comprises the amino acid sequence of SEQ ID NO: 3; a $CDR_{H2}$ comprises the amino acid sequence of SEQ ID NO: 4 and a $CDR_{H3}$ comprises the amino acid sequence of SEQ ID NO: 5. The $CDR_{H1}$, $CDR_{H2}$, and $CDR_{H3}$ sequences are interposed between immunoglobulin FR sequences.

In some embodiments, the antibody comprises (a) an immunoglobulin light chain variable region comprising the structure $CDR_{L1}$-$CDR_{L2}$-$CDR_{L3}$, and (b) an immunoglobulin heavy chain variable region, wherein the IgG light chain variable region and the IgG heavy chain variable region together define a single binding site for binding hNotch3. A CDR$_{L1}$ comprises the amino acid sequence of SEQ ID NO: 7, a CDR$_{L2}$ comprises the amino acid sequence of SEQ ID NO: 8; and a CDR$_{L3}$ comprises the amino acid sequence of SEQ ID NO: 9. The CDR$_{L1}$, CDR$_{L2}$, and CDR$_{L3}$ sequences are interposed between immunoglobulin FR sequences.

In some embodiments, the antibody comprises (a) an immunoglobulin light chain variable region comprising the structure CDR$_{L1}$-CDR$_{L2}$-CDR$_{L3}$, and (b) an immunoglobulin heavy chain variable region, wherein the IgG light chain variable region and the IgG heavy chain variable region together define a single binding site for binding hNotch3. A CDR$_{L1}$ comprises the amino acid sequence of SEQ ID NO: 7 or SEQ ID NO:21, a CDR$_{L2}$ comprises the amino acid sequence of SEQ ID NO: 8 or SEQ ID NO: 22; and a CDR$_{L3}$ comprises the amino acid sequence of SEQ ID NO: 9. The CDR$_{L1}$, CDR$_{L2}$, and CDR$_{L3}$ sequences are interposed between immunoglobulin FR sequences.

In some embodiments, the antibody comprises: (a) an immunoglobulin heavy chain variable region comprising the structure CDR$_{H1}$-CDR$_{H2}$-CDR$_{H3}$ and (b) an immunoglobulin light chain variable region comprising the structure CDR$_{L1}$-CDR$_{L2}$-CDR$_{L3}$, wherein the heavy chain variable region and the light chain variable region together define a single binding site for binding hNotch3. The CDR$_{H1}$ is the amino acid sequence of SEQ ID NO: 3; the CDR$_{H2}$ is the amino acid sequence of SEQ ID NO: 4; and the CDR$_{H3}$ is the amino acid sequence of SEQ ID NO: 5. The CDR$_{L1}$ is the amino acid sequence of SEQ ID NO: 7; the CDR$_{L2}$ is the amino acid sequence of SEQ ID NO: 8; and the CDR$_{L3}$ is the amino acid sequence of SEQ ID NO: 9.

In some embodiments, the antibody comprises: (a) an immunoglobulin heavy chain variable region comprising the structure CDR$_{H1}$-CDR$_{H2}$-CDR$_{H3}$ and (b) an immunoglobulin light chain variable region comprising the structure CDR$_{L1}$-CDR$_{L2}$-CDR$_{L3}$, wherein the heavy chain variable region and the light chain variable region together define a single binding site for binding hNotch3. The CDR$_{H1}$ is the amino acid sequence of SEQ ID NO: 3; the CDR$_{H2}$ is the amino acid sequence of SEQ ID NO: 4; and the CDR$_{H3}$ is the amino acid sequence of SEQ ID NO: 5. The CDR$_{L1}$ is the amino acid sequence of SEQ ID NO: 7 or SEQ ID NO: 21; the CDR$_{L2}$ is the amino acid sequence of SEQ ID NO: 8 or SEQ ID NO: 22; and the CDR$_{L3}$ is the amino acid sequence of SEQ ID NO: 9.

In other embodiments, the antibodies disclosed herein comprise an immunoglobulin heavy chain variable region and an immunoglobulin light chain variable region. In some embodiments, the antibody comprises an immunoglobulin heavy chain variable region comprising the amino acid sequence of SEQ ID NO: 6, and an immunoglobulin light chain variable region.

In other embodiments, the antibody comprises an immunoglobulin light chain variable region comprising the amino acid sequence of SEQ ID NO: 10 and an immunoglobulin heavy chain variable region.

In other embodiments, the antibody comprises an immunoglobulin light chain variable region comprising the amino acid sequence selected from the group consisting of SEQ ID NO: 10, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 37, SEQ ID NO: 38, and SEQ ID NO: 39 and an immunoglobulin heavy chain variable region.

In some embodiments, the antibody comprises an immunoglobulin heavy chain variable region comprising the amino acid sequence of SEQ ID NO: 6, and an immunoglobulin light chain variable region comprising the amino acid sequence selected from the group consisting of SEQ ID NO: 10, SEQ ID NO: 23, SEQ ID NO: 24, SEQ ID NO: 25, SEQ ID NO: 26, SEQ ID NO: 27, SEQ ID NO: 28, SEQ ID NO:29, SEQ ID NO:37, SEQ ID NO:38, and SEQ ID NO:39.

In some embodiments, the antibody comprises an immunoglobulin heavy chain variable region comprising the amino acid sequence of SEQ ID NO: 6, and an immunoglobulin light chain variable region comprising the amino acid sequence of SEQ ID NO: 10.

In some embodiments, the antibody comprises an immunoglobulin heavy chain variable region comprising the amino acid sequence of SEQ ID NO: 6, and an immunoglobulin light chain variable region comprising the amino acid sequence of SEQ ID NO: 10, wherein the amino acid sequence of SEQ ID NO: 10 includes a mutation at one or more of positions 31, 50, 62, 65, 106, and 107. In some embodiments, the amino acid sequence of SEQ ID NO:10 includes one or more mutations selected from the group consisting of N31S, G50A, V62F, T65S F106I, and E107K.

In certain embodiments, the antibodies disclosed herein comprise an immunoglobulin heavy chain and an immunoglobulin light chain. In some embodiments, the antibody comprises an immunoglobulin heavy chain comprising the amino acid sequence of SEQ ID NO: 1, and an immunoglobulin light chain.

In other embodiments, the antibody comprises an immunoglobulin light chain comprising the amino acid sequence of SEQ ID NO: 2, and an immunoglobulin heavy chain.

In other embodiments, the antibody comprises an immunoglobulin light chain comprising an amino acid sequence selected from the group consisting of SEQ ID NO: 2, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 40, SEQ ID NO: 41, and SEQ ID NO: 42 and an immunoglobulin heavy chain.

In some embodiments, the antibody comprises an immunoglobulin heavy chain comprising the amino acid sequence of SEQ ID NO: 1, and an immunoglobulin light chain comprising the amino acid sequence of SEQ ID NO: 2.

In some embodiments, the antibody comprises an immunoglobulin heavy chain comprising the amino acid sequence of SEQ ID NO: 1, and an immunoglobulin light chain comprising an amino acid sequence selected from the group consisting of SEQ ID NO: 2, SEQ ID NO: 30, SEQ ID NO: 31, SEQ ID NO:32, SEQ ID NO: 33, SEQ ID NO: 34, SEQ ID NO: 35, SEQ ID NO: 36, SEQ ID NO: 40, SEQ ID NO: 41, and SEQ ID NO: 42.

In some embodiments, the antibody comprises an immunoglobulin heavy chain comprising the amino acid sequence of SEQ ID NO: 1, and an immunoglobulin light chain comprising the amino acid sequence of SEQ ID NO: 2, wherein the amino acid sequence of SEQ ID NO: 2 includes a mutation at one or more of positions 31, 50, 62, 65, 106, and 107. In some embodiments, the amino acid sequence of SEQ ID NO:10 includes one or more mutations selected from the group consisting of N31S, G50A, V62F, T65S, F106I, and E107K.

In certain embodiments, an isolated antibody that binds hNotch3 comprises an immunoglobulin heavy chain variable region comprising an amino acid sequence that is at least 70%, 75%, 80%, 85%, 90%, 95%, 96%, 97%, 98%, or 99% identical to the entire variable region or the framework region sequence of SEQ ID NO: 6. In certain embodiments, an isolated antibody that binds hNotch3 comprises an immunoglobulin light chain variable region comprising an amino acid sequence that is at least 70%, 75%, 80%, 85%, 90%, 95%, 96%, 97%, 98%, or 99% identical to the entire variable region or the framework region sequence of SEQ ID NO: 10. In certain embodiments, an isolated antibody that binds hNotch3 comprises an immunoglobulin light chain variable region comprising an amino acid sequence that is at least 70%, 75%, 80%, 85%, 90%, 95%, 96%, 97%, 98%, or 99% identical to the entire variable region or the framework region sequence of SEQ ID NO: 23, 24, 25, 26, 27, 28, 29, 37, 38, or 39.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. Sci. USA 87:2264-2268; Altschul, (1993) J. MOL. EVOL. 36, 290-300; Altschul et al., (1997) NUCLEIC ACIDS RES. 25:3389-3402, incorporated by reference) are tailored for sequence similarity searching. For a discussion of basic issues in searching sequence databases see Altschul et al., (1994) NATURE GENETICS 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: –G, Cost to open gap [Integer]: default=5 for nucleotides/11 for proteins; –E, Cost to extend gap [Integer]: default=2 for nucleotides/1 for proteins; –q, Penalty for nucleotide mismatch [Integer]: default=–3; –r, reward for nucleotide match [Integer]: default=1; –e, expect value [Real]: default=10; –W, wordsize [Integer]: default=11 for nucleotides/28 for megablast/3 for proteins; –y, Dropoff (X) for blast extensions in bits: default=20 for blastn/7 for others; –X, X dropoff value for gapped alignment (in bits): default=15 for all programs, not applicable to blastn; and –Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In each of the foregoing embodiments, it is contemplated herein that immunoglobulin heavy chain variable region sequences and/or light chain variable region sequences that together bind hNotch3 may contain amino acid alterations (e.g., at least 1, 2, 3, 4, 5, or 10 amino acid substitutions, deletions, or additions) in the framework regions of the heavy and/or light chain variable regions.

In certain embodiments, the antibody binds hNotch3 with a $K_D$ of 20 nM, 15 nM, 10 nM, 9 nM, 8 nM, 7 nM, 6 nM, 5 nM, 4 nM, 3 nM, 2 nM, 1 nM or lower. Unless otherwise specified, $K_D$ values are determined by surface plasmon resonance or bio-layer interferometry methods under the conditions described in Example 2.

In some embodiments, monoclonal antibodies bind to the same epitope on hNotch3 as that bound by the 28042 antibody. In some embodiments, monoclonal antibodies compete for binding to hNotch3 with the 28042 antibody. For example, monoclonal antibodies may compete for binding to the extracellular domain (ECD) of Notch3 with the 28042 antibody. In another example, monoclonal antibodies may compete for binding to EGF-like repeats 1-11 of human Notch3 with the 28042 antibody (amino acid sequence corresponding to EGF-like repeats 1-11 of human Notch3 is shown in FIG. 3).

Competition assays for determining whether an antibody binds to the same epitope as, or competes for binding with, the 28042 antibody are known in the art. Exemplary competition assays include immunoassays (e.g., ELISA assays, RIA assays), BIAcore analysis, biolayer interferometry, and flow cytometry.

Typically, a competition assay involves the use of an antigen (e.g., a human Notch3 protein or fragment thereof) bound to a solid surface or expressed on a cell surface, a test Notch3-binding antibody and a reference antibody (e.g., the 28042 antibody). The reference antibody is labeled and the test antibody is unlabeled. Competitive inhibition is measured by determining the amount of labeled reference antibody bound to the solid surface or cells in the presence of the test antibody. Usually the test antibody is present in excess (e.g., 1×, 5×, 10×, 20× or 100×). Antibodies identified by competition assay (i.e., competing antibodies) include antibodies binding to the same epitope, or similar (e.g., overlapping) epitopes, as the reference antibody, and antibodies binding to an adjacent epitope sufficiently proximal to the epitope bound by the reference antibody for steric hindrance to occur.

In an exemplary competition assay, a reference Notch3 antibody (e.g., the 28042 antibody) is biotinylated using commercially available reagents. The biotinylated reference antibody is mixed with serial dilutions of the test antibody or unlabeled reference antibody (self-competition control) resulting in a mixture of various molar ratios (e.g., 1×, 5×, 10×, 20× or 100×) of test antibody (or unlabeled reference antibody) to labeled reference antibody. The antibody mixture is added to a human Notch3 (e.g., extracellular domain of human Notch3) polypeptide coated-ELISA plate. The plate then is washed and HRP (horseradish peroxidase)-strepavidin is added to the plate as the detection reagent. The amount of labeled reference antibody bound to the target antigen is detected following addition of a chromogenic substrate (e.g., TMB (3,3',5,5'-tetramethylbenzidine) or ABTS (2,2''-azino-di-(3-ethylbenzthiazoline-6-sulfonate)), which are well-known in the art. Optical density readings (OD units) are measured using a SpectraMax M2 spectrometer (Molecular Devices). OD units corresponding to zero percent inhibition are determined from wells without any competing antibody. OD units corresponding to 100% inhibition, i.e., the assay background are determined from wells without any labeled reference antibody or test antibody. Percent inhibition of labeled reference antibody to Notch3 by the test antibody (or the unlabeled reference antibody) at each concentration is calculated as follows: % inhibition=

(1−(OD units−100% inhibition)/(0% inhibition−100% inhibition))*100. Persons skilled in the art will appreciate that the competition assay can be performed using various detection systems well-known in the art.

A competition assay can be conducted in both directions to ensure that the presence of the label does not interfere or otherwise inhibit binding. For example, in the first direction the reference antibody is labeled and the test antibody is unlabeled, and in the second direction, the test antibody is labeled and the reference antibody is unlabeled.

A test antibody competes with the reference antibody for specific binding to the antigen if an excess of one antibody (e.g., 1×, 5×, 10×, 20× or 100×) inhibits binding of the other antibody, e.g., by at least 50%, 75%, 90%, 95% or 99% as measured in a competitive binding assay.

Two antibodies may be determined to bind to the same epitope if essentially all amino acid mutations in the antigen that reduce or eliminate binding of one antibody reduce or eliminate binding of the other. Two antibodies may be determined to bind to overlapping epitopes if only a subset of the amino acid mutations that reduce or eliminate binding of one antibody reduce or eliminate binding of the other.

II. Antibody Production

Methods for producing antibodies of the invention are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibody. Production of defined gene constructs is within routine skill in the art.

Nucleic acids encoding desired antibodies can be incorporated (ligated) into expression vectors, which can be introduced into host cells through conventional transfection or transformation techniques. Exemplary host cells are *E. coli* cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon, and, optionally, may contain enhancers, and various introns. This expression vector optionally contains sequences encoding all or part of a constant region, enabling an entire, or a part of, a heavy or light chain to be expressed. The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector encoding a polypeptide comprising an entire, or part of, a heavy chain or heavy chain variable region, and another expression vector encoding a polypeptide comprising an entire, or part of, a light chain or light chain variable region).

A polypeptide comprising an immunoglobulin heavy chain variable region or light chain variable region can be produced by growing (culturing) a host cell transfected with an expression vector encoding such variable region, under conditions that permit expression of the polypeptide. Following expression, the polypeptide can be harvested and purified or isolated using techniques known in the art, e.g., affinity tags such as glutathione-S-transferase (GST) and histidine tags.

A monoclonal antibody that binds human Notch3, or an antigen-binding fragment of the antibody, can be produced by growing (culturing) a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment of the antibody) can be harvested and purified or isolated using techniques known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

III. Antibody Modifications

Human monoclonal antibodies can be isolated or selected from phage display libraries including immune, naïve and synthetic libraries. Antibody phage display libraries are known in the art, see, e.g., Hoet et al., NATURE BIOTECH. 23:344-348, 2005; Soderlind et al., NATURE BIOTECH. 18:852-856, 2000; Rothe et al., J. MOL. BIOL. 376:1182-1200, 2008; Knappik et al., J. MOL. BIOL. 296:57-86, 2000; and Krebs et al., J. IMMUNOL. METH. 254:67-84, 2001. When used as a therapeutic, human antibodies isolated by phage display may be optimized (e.g., affinity-matured) to improve biochemical characteristics including affinity and/or specificity, improve biophysical properties including aggregation, stability, precipitation and/or non-specific interactions, and/or to reduce immunogenicity. Affinity-maturation procedures are within ordinary skill in the art. For example, diversity can be introduced into an immunoglobulin heavy chain and/or an immunoglobulin light chain by DNA shuffling, chain shuffling, CDR shuffling, random mutagenesis and/or site-specific mutagenesis.

In some embodiments, isolated human antibodies contain one or more somatic mutations. In these cases, antibodies can be modified to a human germline sequence to optimize the antibody (i.e., a process referred to as germlining).

Generally, an optimized antibody has at least the same, or substantially the same, affinity for the antigen as the non-optimized (or parental) antibody from which it was derived. Preferably, an optimized antibody has a higher affinity for the antigen when compared to the parental antibody.

Human antibody fragments (e.g., parental and optimized variants) can be engineered to contain certain constant (i.e., Fc) regions with a specified effector function (e.g., antibody-dependent cellular cytotoxicity (ADCC)). Human constant regions are known in the art.

If the antibody is for use as a therapeutic, it can be conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

The antibody can be conjugated to an effector moiety such as a small molecule toxin or a radionuclide using standard in vitro conjugation chemistries. If the effector moiety is a polypeptide, the antibody can be chemically conjugated to the effector or joined to the effector as a fusion protein. Construction of fusion proteins is within ordinary skill in the art.

IV. Use of Antibodies

Antibodies disclosed herein can be used to treat various forms of cancer, e.g., leukemia, breast cancer, cervical cancer, colorectal cancer, lung cancer, pancreatic cancer, prostate cancer, gastric cancer, head and neck cancer, endometrial cancer and ovarian cancer. The cancer cells are exposed to a therapeutically effective amount of the antibody so as to inhibit or reduce proliferation of the cancer cells. In some embodiments, the antibodies inhibit cancer cell proliferation by at least 40%, 50%, 60%, 70%, 80%, 90%, 95%, 98%, 99% or 100% relative to a control antibody that does not bind human Notch3 with the same avidity as the 28042 antibody.

In some embodiments, the 28042 antibody or a variant thereof is used in therapy. For example, the 28042 antibody can be used to inhibit tumor growth in a mammal (e.g., a human patient). In some embodiments, use of the antibody to inhibit tumor growth in a mammal comprises administering to the mammal a therapeutically effective amount of the antibody. In other embodiments, the 28042 antibody or a variant thereof can be used for inhibiting proliferation of a tumor cell. In other embodiments, the 28042 antibody or a variant thereof is used to treat or prevent pulmonary arterial hypertension (PAH).

In some embodiments, the disclosed antibodies may inhibit or reduce proliferation of a tumor cell by inhibiting binding of human Notch3 to a ligand, e.g., Jag1, Jag2, DLL1, and DLL4. The disclosed antibodies can be used in a method to inhibit tumor growth in a human patient. The method comprises administering to the patient a therapeutically effective amount of the antibody.

Cancers associated with Notch3 overexpression and/or activation include, but are not limited to, breast cancer, ovarian cancer, prostate cancer, cervical cancer, lung cancer, brain cancer (e.g., glioblastoma, astrocytoma, neuroblastoma), melanomas, gastrointestinal cancers (e.g., colorectal, pancreatic, and gastric), head and neck cancer, sarcomas (e.g. rhabdomyosarcoma, osteosarcoma), and hematopoietic cell cancers, (e.g., multiple myeloma, leukemia, e.g., precursor T acute lymphoblastic leukemia (T-ALL), precursor B acute lymphoblastic leukemia (B-ALL) and B-cell chronic lymphoblastic leukemia (B-CLL)).

As used herein, "treat", "treating" and "treatment" mean the treatment of a disease in a mammal, e.g., in a human. This includes: (a) inhibiting the disease, i.e., arresting its development; and (b) relieving the disease, i.e., causing regression of the disease state.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody, and the disease being treated. Exemplary dosing frequencies are once per day, once per week and once every two weeks. A preferred route of administration is parenteral, e.g., intravenous infusion. Formulation of monoclonal antibody-based drugs is within ordinary skill in the art. In some embodiments, a monoclonal antibody is lyophilized, and then reconstituted in buffered saline, at the time of administration.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods known in the pharmaceutical art. For example, see *Remington's Pharmaceutical Sciences*, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

EXAMPLES

The following Examples are merely illustrative and are not intended to limit the scope or content of the invention in any way.

Example 1: Anti-Notch3 Antibodies

This Example describes the production of anti-hNotch3 monoclonal antibodies.

A. Isolation of Anti-Notch3-Antibodies by Phage Display

Anti-hNotch3 antibodies are isolated from a phage display library constructed from human heavy chain and light chain variable region genes. More specifically, the anti-hNotch3 antibodies are isolated using a phagemid antibody library constructed from human B-cell donor light chain variable and constant genes paired with a single human heavy chain framework consisting of human B-cell donor heavy chain variable region CDR$_3$ genes and a diversity of synthetic heavy chain variable region CDR$_1$ and CDR$_2$ sequences (Dyax Corporation, Burlington, MA).

An anti-hNotch3 antibody (the 28042 antibody) was isolated from a human antibody phage display library following three phage display selection rounds using diminishing amounts of a biotinylated recombinant concatemer of alternating human and murine Notch 3 EGF-like Repeats 1-11 (FIG. 3) as the antigen. 200 pmol of the antigen was used in round one, followed by 50 and 5 pmol in rounds two and three, respectively. At the start of each round of selection, the phage library was depleted with biotinylated human IgG1 Fc. Each round of selection was followed by infection of TG1 *E. coli* (Agilent Technologies, Santa Clara, CA), rescue with M13K07 helper phage (Life Technologies, Grand Island, NY), and phage amplification to enrich the input for each subsequent round. Colonies resulting from the third round of selection were screened by ELISA for binding to both recombinant human and mouse Notch3. All positive clones were sequenced. Clones with unique sequences were expressed as Fabs, Protein A purified, and screened for function. Functional antibodies were converted to full length IgG1 antibodies and further tested for function.

Additionally, non-human light chain residues of the 28042 antibody were individually changed to human germline sequences to create additional light chain variants. For example, the 28042.1 antibody contains the light chain CDR mutation N31S; the 28042.2 antibody contains the light chain CDR mutation G50A; the 28042.3 antibody contains the light chain framework mutation F106I; the 28042.4 antibody contains the light chain framework mutation E107K; the 28042.5 antibody contains the light chain CDR and framework mutations N31S and G50A; the 28042.6 antibody contains the light chain framework mutations F106I and E107K; the 28042.7 antibody contains the light chain CDR and framework mutations N31S, G50A, F106I, E107K; the 28042.8 antibody contains the light chain framework mutation V62F; the 28042.9 antibody contains the light chain framework mutation T65S; and the 28042.10 antibody contains the light chain CDR and framework mutations N31S, G50A, V62F, and T65S. An antibody according to the invention may contain 1 or more of the aforementioned light chain framework and/or CDR mutations.

B. Sequences of Anti-Notch3 Antibodies

The human heavy chains are subcloned into pEE6.4 (Lonza, Basel, Switzerland) via HindIII and EcoRI sites using In-Fusion™ PCR cloning (Clontech, Mountain View, CA). The human kappa light chains are subcloned into pEE14.4 (Lonza) via HindIII and EcoRI sites using In-Fusion™ PCR cloning.

Antibody is either expressed by transient transfection of 293T cells with separate heavy and light chain expressing vectors or by stable transfection of CHOK1SV cells (Lonza) with a single vector expressing heavy and light chains. Antibodies are purified for subsequent analysis. A single expression vector can be constructed by combining pEE6.4 and pEE14.4 based vectors. First, pEE6.4 containing full length human heavy chain cDNA is digested with NotI and SalI to create a fragment containing the hCMV-MIE promoter+full length human heavy chain cDNA+SV40 poly A. This fragment is inserted into the pEE14.4 vector already containing full length human light chain cDNA via NotI/SalI sites, thus creating an expression vector that simultaneously expresses heavy and light chains. The combined heavy and light chain vector is linearized and transfected into CHOK1SV cells. Stable clones are selected in the presence of methionine sulfoximine. Binding of the human antibodies to human Notch3 can be measured as described below.

The nucleic acid sequences encoding and the protein sequences defining variable regions of the human 28042 antibodies are summarized below (amino terminal signal peptide sequences are not shown). In the amino acid sequences, CDR sequences (using the Kabat system) are shown in bold and are underlined.

```
Nucleic Acid Sequence Encoding the Heavy Chain of the 28042 Antibody
                                                         (SEQ ID NO: 11)
gaagttcaattgttagagtctggtggcggtcttgttcagcctggtggttctttacgtctttctt gcgctgcttccggattcactttctctgattacatgatgtcttgggttcgccaagctcctggtaa aggtttggagtgggtttcttggatccgttcttctggtggcactactctttatgctgactccgtt
```

-continued

```
aaaggtcgcttcactatctctagagacaactctaagaatactctctacttgcagatgaacagct taagggctgaggacacagccacatattactgtgcgagagtcggtggtgggaccacgggttatgc ttttgatatctggggccaagggacaatggtcaccgtctcaagcgcctcaacaaaaggaccaagt gtgttcccactcgcccctagcagcaagagtacatccgggggcactgcagcactcggctgcctcg tcaaggattattttccagagccagtaaccgtgagctggaacagtggagcactcacttctggtgt ccatacttttcctgctgtcctgcaaagctctggcctgtactcactcagctccgtcgtgaccgtg ccatcttcatctctgggcactcagacctacatctgtaatgtaaaccacaagcctagcaatacta aggtcgataagcgggtggaacccaagagctgcgacaagactcacacttgtcccccatgccctgc ccctgaacttctgggcggtcccagcgtcttttgttccaccaaagcctaaagatactctgatg ataagtagaacacccgaggtgacatgtgttgttgtagacgtttcccacgaggacccagaggtta agttcaactggtacgttgatggagtcgaagtacataatgctaagaccaagcctagagaggagca gtataatagtacataccgtgtagtcagtgttctcacagtgctgcaccaagactggctcaacggc aaagaatacaaatgcaaagtgtccaacaaagcactcccagcccctatcgagaagactattagta aggcaaaggggcagcctcgtgaaccacaggtgtacactctgccacccagtagagaggaaatgac aaagaaccaagtctcattgacctgcctggtgaaaggcttctaccccagcgacatcgccgttgag tgggagagtaacggtcagcctgagaacaattacaagacaaccccccccagtgctggatagtgacg ggtctttctttctgtacagtaagctgactgtggacaagtcccgctggcagcagggtaacgtctt cagctgttccgtgatgcacgaggcattgcacaaccactacacccagaagtcactgagcctgagc ccagggaag (1353 nucleotides)
```

Protein Sequence Defining the Heavy Chain of the 28042 Antibody
(SEQ ID NO: 1)

Evqllesggglvqpggslrlscaasgftfsdymmswvrqapgkglewvswirssggttlyadsv
kgrftisrdnskntlylqmnslraedtatyycarvqqttqyafdlwgqgtmvtvssastkgps
vfplapssksstsggtaalgclvkdyfpepvtvswnsgaltsgvhtfpavlqssglyslssvvtv
psssslgtqtyicnvnhkpsntkvdkrvepkscdkthtcppcpapellggpsvflfppkpkdtlm
isrtpevtcvvvdvshedpevkfnwyvdgvevhnaktkpreeqynstyrvvsvltvlhqdwlng
keykckvsnkalpapiektiskakgqprepqvytlppsreemtknqvsltclvkgfypsdiave
wesngqpennykttppvldsdgsfflyskltvdksrwqqgnvfscsvmhealhnhytqkslsls
pgk (451 amino acids)

Nucleic Acid Sequence Encoding the Heavy Chain Variable Region of the 28042 Antibody
(SEQ ID NO: 17)

```
gaagttcaat tgttagagtc tggtggcggt cttgttcagc ctggtggttc     50
tttacgtctt tcttgcgctg cttccggatt cactttctct gattacatga    100
tgtcttgggt tcgccaagct cctggtaaag gtttggagtg gtttcttgg    150 atccgttctt ctggtggcac tactctttat gctgactccg ttaaaggtcg    200
cttcactatc tctagagaca actctaagaa tactctctac ttgcagatga    250
acagcttaag ggctgaggac acagccacat attactgtgc gagagtcggt    300
ggtgggacca cgggttatgc ttttgatatc tggggccaag gacaatggt    350 caccgtctca agc                                              363
```

Protein Sequence Defining the Heavy Chain Variable Region of the 28042 Antibody
(SEQ ID NO: 6)

```
evqllesggg lvqpggslrl scaasgftfs dymms wvrqa pgkglewvsw  50 irssggttly adsvkg rfti srdnskntly lqmnslraed tatyycar vg  100 ggttgyafdi wgqgtmvtvs s                                  121
```

Nucleic Acid Sequence Encoding the Kappa Chain of the 28042 Antibody
(SEQ ID NO: 12)

```
gacatccaga tgacccagtc tccatcctcc ctgtctgcat ctgtaggaga  50
cagagtcacc atcacttgcc gggcaagtca gagcattagc aactatttaa  100
attggtatca gcagaaacca gggaaagccc ctaagctcct gatctatggt  150
gcatccagtc tgcaaagtgg ggtcccatca agggtcagtg gcactggatc  200
tgggacagat ttcactctta ccatcagcag tctgcaacct gaagattttg  250
caacttacta ctgtcaacag agttacagtc cctcattcac tttcggccct  300
gggaccaaag tggatttcga acgaactgtg gctgcaccat ctgtgttcat  350
ctttccacca agtgatgagc aactgaagtc tggtactgct tcagtcgtgt  400
gtctgctgaa caatttctac cctcgagaag ccaaagtcca atggaaggta  450
gacaacgcac tgcagtccgg caatagccaa gaatcagtta ccgaacagga  500
ttcaaaggac agtacatatt ccctgagcag cactctgacc ctgtcaaagg  550
ccgattacga gaaacacaag gtctatgctt gcgaagtgac acatcaggga  600
ctgtccagcc cagtgacaaa atcttttaac cgtggggagt gt           642
```

Protein Sequence Defining the Kappa Chain of the 28042 Antibody
(SEQ ID NO: 2)

```
digmtgspss lsasvgdrvt itc rasqsis nyln wyqqkp gkapklliyg  50 aslqs gvps rvsgtgsgtd ftltisslqp edfatyyc qq syspsft fgp  100 gtkvdfertv aapsvfifpp sdeqlksgta svvcllnnfy preakvqwkv  150 dnalqsgnsq esvtegdskd styslsstlt lskadyekhk vyacevthqg  200 lsspvtksfn rgec                                          214
```

Nucleic Acid Sequence Encoding the Kappa Chain Variable Region of the 28042 Antibody
(SEQ ID NO: 18)

```
gacatccaga tgacctagtc tccatcctcc ctgtctgcat ctgtaggaga  50
cagagtcacc atcacttgcc gggcaagtca gagcattagc aactatttaa  100
attggtatca gcagaaacca gggaaagccc ctaagctcct gatctatggt  150
gcatccagtc tgcaaagtgg ggtcccatca agggtcagtg gcactggatc  200
tgggacagat ttcactctta ccatcagcag tctgcaacct gaagattttg  250
caacttacta ctgtcaacag agttacagtc cctcattcac tttcggccct  300
gggaccaaag tggatttcga a                                  321
```

Protein Sequence Defining the Kappa Chain Variable Region of the 28042 Antibody
(SEQ ID NO: 10)

```
diqmtqspss lsasvgdrvt itc rasqsis nyln wyqqkp gkapklliyg  50 aslqs gvps rvsgtgsgtd ftltisslqp edfatyyc qq syspsft fgp  100 gtkvdfe                                                  107
```

The amino acid sequence defining the immunoglobulin heavy chain variable region for the antibodies produced in Example 1 is shown in FIG. 4. Amino terminal signal peptide sequences (for proper expression/secretion) are not shown. CDR$_1$, CDR$_2$, and CDR$_3$ (using the Kabat system) are identified by boxes.

The amino acid sequences defining the immunoglobulin light chain variable regions for the antibodies in Example 1 are aligned in FIG. 5. Amino terminal signal peptide sequences (for proper expression/secretion) are not shown. CDR₁, CDR₂ and CDR₃ are identified by boxes.

Table 1 is a concordance chart showing the SEQ ID NO. of each sequence discussed in this Example.

TABLE 1

| SEQ. ID NO. | Nucleic Acid or Protein |
|---|---|
| 11 | Heavy Chain of the 28042 Antibody - nucleic acid |
| 1 | Heavy Chain of the 28042 Antibody - protein |
| 17 | Heavy Chain Variable Region of the 28042 Antibody - nucleic acid |
| 6 | Heavy Chain Variable Region of the 28042 Antibody - protein |
| 12 | Kappa (light) Chain of the 28042 Antibody - nucleic acid |
| 2 | Kappa (light) Chain of the 28042 Antibody - protein |
| 18 | Kappa (light) Chain Variable Region of the 28042 Antibody - nucleic acid |
| 10 | Kappa (light) Chain Variable Region of the 28042 Antibody - protein |

Human monoclonal antibody 28042 heavy chain CDR sequences (Kabat definition) are shown in Table 2.

TABLE 2

| | CDR1 | CDR2 | CDR3 |
|---|---|---|---|
| Kabat | DYMMS (SEQ ID NO: 3) | WIRSSGGTTLYADSVKG (SEQ ID NO: 4) | VGGGTTGYAFDI (SEQ ID NO: 5) |

Human monoclonal antibody 28042 Kappa light chain CDR sequences (Kabat definition) are shown in Table 3.

TABLE 3

| | CDR1 | CDR2 | CDR3 |
|---|---|---|---|
| Kabat | RASQSISNYLN (SEQ ID NO: 7) | GASSLQS (SEQ ID NO: 8) | QQSYSPSFT (SEQ ID NO: 9) |

```
Nucleic Acid Sequence Encoding the Human IgG1 Heavy Chain Constant Region
                                                           (SEQ ID NO: 16)
      gcctcaacaa aaggaccaag tgtgttccca ctcgcccta gcagcaagag    50 tacatccggg ggcactgcag cactcggctg cctcgtcaag gattattttc   100
cagagccagt aaccgtgagc tggaacagtg gagcactcac ttctggtgtc   150
catacttttc ctgctgtcct gcaaagctct ggcctgtact cactcagctc   200
cgtcgtgacc gtgccatctt catctctggg cactcagacc tacatctgta   250
atgtaaacca caagcctagc aatactaagg tcgataagcg ggtggaaccc    300
aagagctgcg acaagactca cacttgtccc ccatgccctg ccctgaact    350 tctgggcggt cccagcgtct ttttgttccc accaaagcct aaagatactc    400
tgatgataag tagaacaccc gaggtgacat gtgttgttgt agacgtttcc    450
cacgaggacc cagaggttaa gttcaactgg tacgttgatg gagtcgaagt    500
acataatgct aagaccaagc ctagagagga gcagtataat agtacatacc    550
gtgtagtcag tgttctcaca gtgctgcacc aagactggct caacggcaaa   600
gaatacaaat gcaaagtgtc caacaaagca ctcccagccc tatcgagaa    650 gactattagt aaggcaaagg ggcagcctcg tgaaccacag gtgtacactc    700
tgccacccag tagagaggaa atgacaaaga accaagtctc attgacctgc    750
ctggtgaaag gcttctaccc cagcgacatc gccgttgagt gggagagtaa    800
cggtcagcct gagaacaatt acaagacaac cccccagtg ctggatagtg    850 acgggtcttt ctttctgtac agtaagctga ctgtggacaa gtcccgctgg    900
cagcagggta acgtcttcag ctgttccgtg atgcacgagg cattgcacaa    950
ccactacacc cagaagtcac tgagcctgag cccagggaag                990

Protein Sequence Defining the Human IgG1 Heavy Chain Constant Region
                                                           (SEQ ID NO: 13)
      astkgpsvfp lapsskstsg gtaalgclvk dyfpepvtvs wnsgaltsgv   50 htfpavlqss glyslssvvt vpssslgtqt yicnvnhkps ntkvdkrvep   100 kscdkthtcp pcpapellgg psvflfppkp kdtlmisrtp evtcvvvdvs   150 hedpevkfnw yvdgvevhna ktkpreeqyn styrvvsvlt vlhqdwlngk   200
```

```
eykckvsnka lpapiektis kakgqprepq vytlppsree mtknqvsltc 250 lvkgfypsdi avewesngqp ennykttppv ldsdgsffly skltvdksrw 300 qqgnvfscsv mhealhnhyt qkslslspgk                     330
```

Nucleic Acid Sequence Encoding the Human Kappa Light Chain Constant Region
of the 28042 Antibody (SEQ ID NO: 15)

```
cgaactgtgg ctgcaccatc tgtgttcatc tttccaccaa gtgatgagca  50
actgaagtct ggtactgctt cagtcgtgtg tctgctgaac aatttctacc 100
ctcgagaagc caaagtccaa tggaaggtag acaacgcact gcagtccggc 150
aatagccaag aatcagttac cgaacaggat tcaaaggaca gtacatattc 200
cctgagcagc actctgaccc tgtcaaaggc cgattacgag aaacacaagg 250
tctatgcttg cgaagtgaca catcagggac tgtccagccc agtgacaaaa 300
tcttttaacc gtggggagtg t                              321
```

Protein Sequence Defining the Human Kappa Light Chain Constant Region of
the 28042 Antibody_

(SEQ ID NO: 14)

```
rtvaapsvfi fppsdeqlks gtasvvclln nfypreakvq wkvdnalqsg  50 nsqesvteqd skdstyslss tltlskadye khkvyacevt hqglsspvtk 100 sfnrgec                                              107
```

Table 4 is a concordance chart showing the SEQ ID NO. of each sequence discussed in this Example.

TABLE 4

| SEQ ID NO. | Nucleic Acid or Protein |
|---|---|
| 11 | 28042 Heavy Human Variable Region (SEQ ID NO: 17) + Human IgG1 Constant Region (SEQ ID NO: 16) - nucleic acid |
| 1 | 28042 Heavy Human Variable Region (SEQ ID NO: 6) + Human IgG1 Constant Region (SEQ ID NO: 13) - protein |
| 12 | 28042 Kappa Human Variable Region (SEQ ID NO: 18) + Human Kappa Constant Region (SEQ ID NO: 15) - nucleic acid |
| 2 | 28042 Kappa Human Variable Region (SEQ ID NO: 10) + Human Kappa Constant Region (SEQ ID NO: 14) - protein |

The following sequences relate to variants of the 28042 antibody where certain residues in the framework region have been modified via germlining. The CDR sequences are underlined.

Protein Sequence Defining the Kappa Chain Variable Region of the
28042.1 Antibody (SEQ ID NO: 23)

```
diqmtqspss lsasvgdrvt itcrasqsis Sylnwyqqkp gkapklliyg  50 asslqsgvps rvsgtgsgtd ftltisslqp edfatyycqq syspsftfgp 100 gtkvdfe                                              107
```

Protein Sequence Defining the Kappa Chain Variable Region of the
28042.2 Antibody (SEQ ID NO: 24)

```
diqmtqspss lsasvgdrvt itcrasqsis nylnwyqqkp gkapklliyA  50 asslqsgvps rvsgtgsgtd ftltisslqp edfatyycqq syspsftfgp 100 gtkvdfe                                              107
```

Protein Sequence Defining the Kappa Chain Variable Region of the
28042.3 Antibody (SEQ ID NO: 25)

```
diqmtqspss lsasvgdrvt itcrasqsis nylnwyqqkp gkapklliyg  50 asslqsgvps rvsgtgsgtd ftltisslqp edfatyycqq syspsftfgp 100 gtkvdIe                                              107
```

Protein Sequence Defining the Kappa Chain Variable Region of the 28042.4 Antibody
(SEQ ID NO: 26)
diqmtqspss lsasvgdrvt itcrasqsis nylnwyqqkp gkapklliyg 50 asslqsgvps rvsgtgsgtd ftltisslqp edfatyycqq syspsftfgp 100 gtkvdfK 107

Protein Sequence Defining the Kappa Chain Variable Region of the 28042.5 Antibody
(SEQ ID NO: 27)
diqmtqspss lsasvgdrvt itcrasqsis Sylnwyqqkp gkapklliyA 50 asslqsgvps rvsgtgsgtd ftltisslqp edfatyycqq syspsftfgp 100 gtkvdfe 107

Protein Sequence Defining the Kappa Chain Variable Region of the 28042.6 Antibody
(SEQ ID NO: 28)
diqmtqspss lsasvgdrvt itcrasqsis nylnwyqqkp gkapklliyg 50 asslqsgvps rvsgtgsgtd ftltisslqp edfatyycqq syspsftfgp 100 gtkvdIK 107

Protein Sequence Defining the Kappa Chain Variable Region of the 28042.7 Antibody
(SEQ ID NO: 29)
diqmtqspss lsasvgdrvt itcrasqsis Sylnwyqqkp gkapklliyA 50 asslqsgvps rvsgtgsgtd ftltisslqp edfatyycqq syspsftfgp 100 gtkvdIK 107

Protein Sequence Defining the Kappa Chain Variable Region of the 28042.8 Antibody
(SEQ ID NO: 37)
diqmtqspss lsasvgdrvt itcrasqsis nylnwyqqkp gkapklliyg 50 asslqsgvps rFsgtgsgtd ftltisslqp edfatyycqq syspsftfgp 100 gtkvdfe 107

Protein Sequence Defining the Kappa Chain Variable Region of the 28042.9 Antibody
(SEQ ID NO: 38)
diqmtqspss lsasvgdrvt itcrasqsis nylnwyqqkp gkapklliyg 50 asslqsgvps rvsgSgsgtd ftltisslqp edfatyycqq syspsftfgp 100 gtkvdfe 107

Protein Sequence Defining the Kappa Chain Variable Region of the 28042.10 Antibody
(SEQ ID NO: 39)
diqmtqspss lsasvgdrvt itcrasqsis Sylnwyqqkp gkapklliyA 50 asslqsgvps rFsgSgsgtd ftltisslqp edfatyycqq syspsftfgp 100 gtkvdfe 107

Protein Sequence Defining the Kappa Chain of the 28042.1 Antibody
(SEQ ID NO: 30)
diqmtqspss lsasvgdrvt itcrasqsis Sylnwyqqkp gkapklliyg 50 asslqsgvps rvsgtgsgtd ftltisslqp edfatyycqq syspsftfgp 100 gtkvdfertv aapsvfifpp sdeqlksgta svvellnnfy preakvqwkv 150 dnalqsgnsq esvteqdskd styslsstlt lskadyekhk vyacevthqg 200 lsspvtksfn rgec 214

Protein Sequence Defining the Kappa Chain of the 28042.2 Antibody
(SEQ ID NO: 31)
diqmtqspss lsasvgdrvt itcrasqsis nylnwyqqkp gkapklliyA 50 asslqsgvps rvsgtgsgtd ftltisslqp edfatyycqq syspsftfgp 100

```
gtkvdfertv aapsvfifpp sdeqlksgta svvellnnfy preakvqwkv  150 dnalqsgnsq esvteqdskd styslsstlt lskadyekhk vyacevthqg  200 lsspvtksfn rgec                                         214
```

Protein Sequence Defining the Kappa Chain of the 28042.3 Antibody (SEQ ID NO: 32)
```
digmtgspss lsasvgdrvt itcrasqsis nylnwyqqkp gkapklliyg  50 asslqsgvps rvsgtgsgtd ftltisslqp edfatyycqq syspsftfgp  100 gtkvdIertv aapsvfifpp sdeqlksgta svvellnnfy preakvqwkv  150 dnalqsgnsq esvteqdskd styslsstlt lskadyekhk vyacevthqg  200 lsspvtksfn rgec                                         214
```

Protein Sequence Defining the Kappa Chain of the 28042.4 Antibody (SEQ ID NO: 33)
```
digmtgspss lsasvgdrvt itcrasqsis nylnwyqqkp gkapklliyg  50 asslqsgvps rvsgtgsgtd ftltisslqp edfatyycqq syspsftfgp  100 gtkvdfKrtv aapsvfifpp sdeqlksgta svvellnnfy preakvqwkv  150 dnalqsgnsq esvteqdskd styslsstlt lskadyekhk vyacevthqg  200 lsspvtksfn rgec                                         214
```

Protein Sequence Defining the Kappa Chain of the 28042.5 Antibody (SEQ ID NO: 34)
```
digmtgspss lsasvgdrvt itcrasqsis Sylnwyqqkp gkapklliyA  50 asslqsgvps rvsgtgsgtd ftltisslqp edfatyycqq syspsftfgp  100 gtkvdfertv aapsvfifpp sdeqlksgta svvellnnfy preakvqwkv  150 dnalqsgnsq esvteqdskd styslsstlt lskadyekhk vyacevthqg  200 lsspvtksfn rgec                                         214
```

Protein Sequence Defining the Kappa Chain of the 28042.6 Antibody (SEQ ID NO: 35)
```
digmtgspss lsasvgdrvt itcrasqsis nylnwyqqkp gkapklliyg  50 asslqsgvps rvsgtgsgtd ftltisslqp edfatyycqq syspsftfgp  100 gtkvdIKrtv aapsvfifpp sdeqlksgta svvellnnfy preakvqwkv  150 dnalqsgnsq esvteqdskd styslsstlt lskadyekhk vyacevthqg  200 lsspvtksfn rgec                                         214
```

Protein Sequence Defining the Kappa Chain of the 28042.7 Antibody (SEQ ID NO: 36)
```
digmtgspss lsasvgdrvt itcrasqsis Sylnwyqqkp gkapklliyA  50 asslqsgvps rvsgtgsgtd ftltisslqp edfatyycqq syspsftfgp  100 gtkvdIKrtv aapsvfifpp sdeqlksgta svvellnnfy preakvqwkv  150 dnalqsgnsq esvtegdskd styslsstlt lskadyekhk vyacevthqg  200 lsspvtksfn rgec                                         214
```

Protein Sequence Defining the Kappa Chain of the 28042.8 Antibody (SEQ ID NO: 40)
```
digmtgspss lsasvgdrvt itcrasqsis nylnwyqqkp gkapklliyg  50 asslqsgvps rFsgtgsgtd ftltisslqp edfatyycqq syspsftfgp  100 gtkvdfertv aapsvfifpp sdeqlksgta svvellnnfy preakvqwkv  150 dnalqsgnsq esvtegdskd styslsstlt lskadyekhk vyacevthqg  200 lsspvtksfn rgec                                         214
```

```
Protein Sequence Defining the Kappa Chain of the 28042.9 Antibody
                                                 (SEQ ID NO: 41)
digmtgspss lsasvgdrvt itcrasqsis nylnwyqqkp gkapklliyg  50 asslqsgvps rvsgSgsgtd ftltisslqp edfatyycqq syspsftfgp 100 gtkvdfertv aapsvfifpp sdeqlksgta svvellnnfy preakvqwkv 150 dnalqsgnsq esvtegdskd styslsstlt lskadyekhk vyacevthqg 200 lsspvtksfn rgec                                        214

Protein Sequence Defining the Kappa Chain of the 28042.10
Antibody
                                                 (SEQ ID NO: 42)
digmtgspss lsasvgdrvt itcrasqsis SylnwyqqkpgkapklliyA  50 asslqsgvps rFsgSgsgtd ftltisslqp edfatyycqq syspsftfgp 100 gtkvdfertv aapsvfifpp sdeqlksgta svvellnnfy preakvqwkv 150 dnalqsgnsq esvtegdskd styslsstlt lskadyekhk vyacevthqg 200 lsspvtksfn rgec                                        214
```

Table 5 provides the heavy chain and light chain full length sequences for the 28042 antibody and antibody variants 28042.1-28042.10.

TABLE 5

| Antibody Name | Heavy Chain Protein Sequence | Light Chain Protein Sequence |
|---|---|---|
| 28042 | SEQ ID NO: 1 | SEQ ID NO: 2 |
| 28042.1 | SEQ ID NO: 1 | SEQ ID NO: 30 |
| 28042.2 | SEQ ID NO: 1 | SEQ ID NO: 31 |
| 28042.3 | SEQ ID NO: 1 | SEQ ID NO: 32 |
| 28042.4 | SEQ ID NO: 1 | SEQ ID NO: 33 |
| 28042.5 | SEQ ID NO: 1 | SEQ ID NO: 34 |
| 28042.6 | SEQ ID NO: 1 | SEQ ID NO: 35 |
| 28042.7 | SEQ ID NO: 1 | SEQ ID NO: 36 |
| 28042.8 | SEQ ID NO: 1 | SEQ ID NO: 40 |
| 28042.9 | SEQ ID NO: 1 | SEQ ID NO: 41 |
| 28042.10 | SEQ ID NO: 1 | SEQ ID NO: 42 |

Table 6 provides combinations of heavy chain variable region protein sequences, heavy chain constant region sequences, light chain variable region sequences and light chain constant region sequences for the 28042 antibody and antibody variants 28042.1-28042.10.

TABLE 6

| Antibody Name | Heavy Chain Variable Protein Sequence | Heavy Chain Constant Region Sequence | Light Chain Variable Region Sequence | Light Chain Constant Region Sequence |
|---|---|---|---|---|
| 28042 | SEQ ID NO: 6 | SEQ ID NO: 13 | SEQ ID NO: 10 | SEQ ID NO: 14 |
| 28042.1 | SEQ ID NO: 6 | SEQ ID NO: 13 | SEQ ID NO: 23 | SEQ ID NO: 14 |
| 28042.2 | SEQ ID NO: 6 | SEQ ID NO: 13 | SEQ ID NO: 24 | SEQ ID NO: 14 |
| 28042.3 | SEQ ID NO: 6 | SEQ ID NO: 13 | SEQ ID NO: 25 | SEQ ID NO: 14 |
| 28042.4 | SEQ ID NO: 6 | SEQ ID NO: 13 | SEQ ID NO: 26 | SEQ ID NO: 14 |
| 28042.5 | SEQ ID NO: 6 | SEQ ID NO: 13 | SEQ ID NO: 27 | SEQ ID NO: 14 |
| 28042.6 | SEQ ID NO: 6 | SEQ ID NO: 13 | SEQ ID NO: 28 | SEQ ID NO: 14 |
| 28042.7 | SEQ ID NO: 6 | SEQ ID NO: 13 | SEQ ID NO: 29 | SEQ ID NO: 14 |
| 28042.8 | SEQ ID NO: 6 | SEQ ID NO: 13 | SEQ ID NO: 37 | SEQ ID NO: 14 |
| 28042.9 | SEQ ID NO: 6 | SEQ ID NO: 13 | SEQ ID NO: 38 | SEQ ID NO: 14 |
| 28042.10 | SEQ ID NO: 6 | SEQ ID NO: 13 | SEQ ID NO: 39 | SEQ ID NO: 14 |

Table 7 discloses the CDR sequences for antibody 28042 and variants 28042.1-28042.10.

TABLE 7

| Antibody | $CDR_{H1}$ | $CDR_{H2}$ | $CDR_{H3}$ | $CDR_{L1}$ | $CDR_{L2}$ | $CDR_{L3}$ |
|---|---|---|---|---|---|---|
| 28042 | SEQ ID NO: 3 | SEQ ID NO: 4 | SEQ ID NO: 5 | SEQ ID NO: 7 | SEQ ID NO: 8 | SEQ ID NO: 9 |
| 28042.1 | SEQ ID NO: 3 | SEQ ID NO: 4 | SEQ ID NO: 5 | SEQ ID NO: 21 | SEQ ID NO: 8 | SEQ ID NO: 9 |
| 28042.2 | SEQ ID NO: 3 | SEQ ID NO: 4 | SEQ ID NO: 5 | SEQ ID NO: 7 | SEQ ID NO: 22 | SEQ ID NO: 9 |
| 28042.3 | SEQ ID NO: 3 | SEQ ID NO: 4 | SEQ ID NO: 5 | SEQ ID NO: 7 | SEQ ID NO: 8 | SEQ ID NO: 9 |
| 28042.4 | SEQ ID NO: 3 | SEQ ID NO: 4 | SEQ ID NO: 5 | SEQ ID NO: 7 | SEQ ID NO: 8 | SEQ ID NO: 9 |
| 28042.5 | SEQ ID NO: 3 | SEQ ID NO: 4 | SEQ ID NO: 5 | SEQ ID NO: 21 | SEQ ID NO: 22 | SEQ ID NO: 9 |
| 28042.6 | SEQ ID NO: 3 | SEQ ID NO: 4 | SEQ ID NO: 5 | SEQ ID NO: 7 | SEQ ID NO: 8 | SEQ ID NO: 9 |
| 28042.7 | SEQ ID NO: 3 | SEQ ID NO: 4 | SEQ ID NO: 5 | SEQ ID NO: 21 | SEQ ID NO: 22 | SEQ ID NO: 9 |
| 28042.8 | SEQ ID NO: 3 | SEQ ID NO: 4 | SEQ ID NO: 5 | SEQ ID NO: 7 | SEQ ID NO: 8 | SEQ ID NO: 9 |

TABLE 7-continued

| Antibody | CDR$_{H1}$ | CDR$_{H2}$ | CDR$_{H3}$ | CDR$_{L1}$ | CDR$_{L2}$ | CDR$_{L3}$ |
|---|---|---|---|---|---|---|
| 28042.9 | SEQ ID NO: 3 | SEQ ID NO: 4 | SEQ ID NO: 5 | SEQ ID NO: 7 | SEQ ID NO: 8 | SEQ ID NO: 9 |
| 28042.10 | SEQ ID NO: 3 | SEQ ID NO: 4 | SEQ ID NO: 5 | SEQ ID NO: 21 | SEQ ID NO: 22 | SEQ ID NO: 9 |

Example 2: Binding Affinities

The binding affinity and kinetics of binding of the 28042 antibody to recombinant human Notch3 extracellular domain (containing EGF like domains 1-11) Fc fusion protein (rhNotch3-Fc (R&D Systems, Inc., Minneapolis, MN)) can be measured by surface plasmon resonance using a Biacore® T100 instrument (GE Healthcare, Piscataway, NJ).

Goat anti-human IgG is immobilized on carboxymethylated dextran CM4 sensor chips (GE Healthcare) by amine coupling, according to a standard protocol. Analyses are performed at 25° C. and 37° C. using PBS containing 0.05% surfactant P20 as running buffer. The antibody is captured in individual flow cells at a flow rate of 10 µl/minute. Injection time is varied for each antibody to yield an Rmax between 30 and 60 resonance units (RU). 250 µg/mL human IgG Fc is injected to block non-specific binding of Fc (from the Notch3 fusion protein) to the capture antibody. Buffer or rhNotch3-Fc diluted in running buffer is injected sequentially over a reference surface (no antibody captured) and the active surface (antibody to be tested) for 240 seconds at 60 µL/minute. The dissociation phase is monitored for up to 1500 seconds. The surface is then regenerated with two 60-second injections of 10 mM Glycine-HCl, pH 2.25, at a flow rate of 30 µL/minute. The rhNotch3-Fc concentration range tested is 100 nM to 3.125 nM (2 fold dilution).

Kinetic parameters can be determined using the kinetic function of the BIAevaluation software (GE Healthcare) with double reference subtraction. Kinetic parameters for the antibody, $k_a$ (association rate constant), $k_d$ (dissociation rate constant) and $K_D$ (equilibrium dissociation constant) are determined.

Kinetic values of the monoclonal antibody 28042 on rhNotch3-Fc at 25° C. and 37° C. are summarized in Table 8.

TABLE 8

Antibody Binding to rhNotch3-Fc

| Temperature | $k_a$ (1/Ms) | $k_d$ (1/s) | $K_D$ (M) |
|---|---|---|---|
| 25° C. | 1.77E+05 | 2.99E−04 | 2.55E−09 |
| 37° C. | 9.47E+04 | 3.96E−04 | 4.18E−09 |

The data in Table 8 demonstrate that the 28042 antibody binds rhNotch3-Fc with a $K_D$ of about 1-10 nM, 10 nM, 9 nM, 8 nM, 7 nM, 6 nM, 5 nM, 4 nM, 3 nM, 2 nM, 1 nM, 900 pM, 850 pM, 800 pM, 750 pM, 700 pM, 650 pM, 600 pM, 500 pM, 400 pM, 300 pM, or 200 pM or less.

Binding to cell surface human Notch3 by the antibody 28042 can be measured at 4° C., using Fluorescence Activated Cell Sorting (FACS). CHO N3 (Flp-In-CHO cells (Invitrogen) stably transfected with human Notch3), HCC2429 cells, and RL-952 cells expressing human Notch3 are washed once with PBS containing calcium chloride and magnesium chloride (Invitrogen) and harvested using cell dissociation buffer (Invitrogen). Cells are washed a second time with PBS and resuspended in FACS buffer (PBS with 0.5% BSA (Sigma-Aldrich)) for a final cell concentration of 250,000 cells per well into a 96-well v-bottom plate. Purified antibodies are diluted in FACS buffer over a concentration range of 100 nM to 0 nM. Cells are then incubated at 4° C. with 100 µL of antibody for one hour, washed with FACS buffer twice, and resuspended in 100 µL of goat-anti mouse PE-conjugated antibody (Jackson Immuno Research). Cells are incubated at 4° C. for 30 minutes in the dark, washed once with FACS buffer, and then analyzed using a Beckman Coulter Cytomics FC 500 instrument. The geometric mean of the florescent intensity then is calculated for each antibody concentration. These values then are entered into Prism software (GraphPad, La Jolla, CA) and used to generate a binding curve by plotting geometric mean versus antibody concentration. From the binding curve, the following equation is used to calculate the $K_D$ and $K_D$ range of 28042 antibody binding to human Notch3 on the cell surface of the three cell lines.

$$Y=B\max*X/(K_D+X)$$  Equation: One site binding (hyperbola)

* describes the binding of a ligand to a receptor that follows the law of mass action. Bmax is the maximal binding, and $K_D$ is the concentration of ligand required to reach half-maximal binding.

The results for the 28042 antibody are summarized in Table 9.

TABLE 9

Binding to hNotch3 on Cell Surface

| $K_D$ (nM) | $K_D$ Range (nM) |
|---|---|
| 2.723 | 1.794 to 3.652 |

The data in Table 9 demonstrate that the 28042 antibody binds rhNotch3-Fc with a $K_D$ of about 1-10 nM, 10 nM, 9 nM, 8 nM, 7 nM, 6 nM, 5 nM, 4 nM, 3 nM, 2 nM, 1 nM, 900 pM, 850 pM, 800 pM, 750 pM, 700 pM, 650 pM, 600 pM, 500 pM, 400 pM, 300 pM, or 200 pM or less.

$K_D$ values for the binding of the 28042 and 28042.1-28042.7 antibodies to cynoNotch3 was tested according to a similar protocol as described above for 28042 antibody binding to hNotch3, and the results are shown in Table 10.

TABLE 10

Binding to cynoNotch3 monomer at 25° C.

| Antibody | $K_D$ (M) |
|---|---|
| 28042.1 | 5.35E−09 |
| 28042.2 | 2.14E−07 |
| 28042.3 | 2.65E−07 |
| 28042.4 | 3.36E−07 |
| 28042.5 | 2.11E−07 |
| 28042.6 | 1.92E−07 |
| 28042.7 | 2.51E−07 |
| 28042 | 8.06E−07 |

Example 3: Binding Specificity

In this example, the binding specificity of the 28042 antibody for human Notch1, human Notch2, human Notch3, or murine Notch3 proteins is described.

The specificity of the 28042 antibody binding for Notch-Fc fusion proteins can be determined using surface plasmon resonance using a Biacore® T100 instrument (GE Healthcare, Piscataway, NJ). Rabbit anti-mouse IgGs (GE Healthcare) are immobilized on carboxymethylated dextran CM4 sensor chips (GE Healthcare) by amine coupling, according to a standard protocol. Analyses are performed at 25° C. and 37° C. using PBS containing 0.05% surfactant P20 as running buffer. The antibody is captured in individual flow cells at a flow rate of 10 µL/minute. Injection time is varied for each antibody to yield an Rmax between 30 and 60 RU. 250 µg/mL human IgG Fc is injected to block non-specific binding of Fc (from the Notch3 fusion protein) to the capture antibody. Buffer or rhNotch1-Fc (R&D Systems, Minneapolis, MN; Cat. No. 3647-TK-050), rhNotch2-Fc (R&D Cat. No. 3735-NT-050), and rhNotch3-Fc (R&D Cat. No. 1559-NT-050), diluted in running buffer is injected sequentially over a reference surface (no antibody captured) and the active surface (antibody to be tested) for 240 seconds at 60 µL/minute. The dissociation phase is monitored for up to 1500 seconds. The surface is then regenerated with two 60-second injections of 10 mM Glycine-HCl, pH 2.25, at a flow rate of 30 µL/minute. The rhNotch3-Fc, rhNotch2-Fc, and rhNotch1-Fc concentration range tested are 100 nM to 3.125 nM (2 fold dilution).

Figure 6:
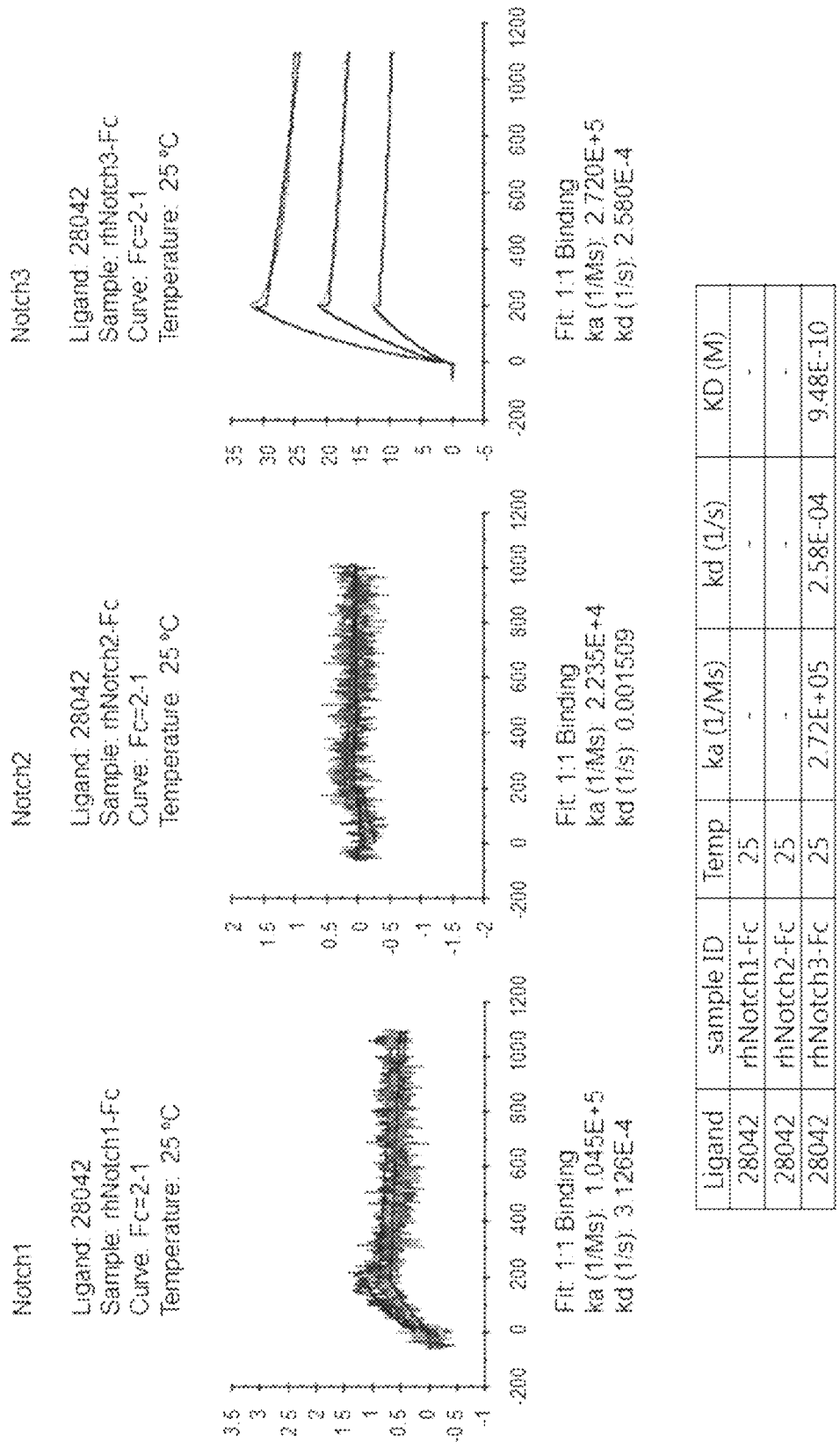
FIG. 6 shows the binding of the 28042 antibody to Fc fusion proteins of the extracellular domains of Notch1, Notch2, and Notch3, as observed by surface plasmon resonance (SPR). Binding was measured at three different dilutions. The results demonstrate that the binding affinity of the 28042 antibody for Notch3 is high while there is no appreciable binding of the 28042 antibody to Notch1 or Notch2.

As shown in FIG. 6, the specificity of the 28042 antibody binding to the extracellular domains of Notch1-Fc, Notch2-Fc, and Notch3-Fc fusion proteins was measured at three different dilutions by surface plasmon resonance. As shown in FIG. 6, the binding affinity of the 28042 antibody for Notch3 is high while there is no appreciable binding of the 28042 antibody to Notch1 or Notch2.

To determine the specificity of binding to cell surface Notch proteins, stable cells lines expressing Notch receptors are produced by transfecting FlpIn™ CHO or FlpIn™ 293 cells (Life Technologies, Grand Island, NY) with full length human Notch1, Notch2, Notch3, or full length murine Notch3 cDNAs cloned into the pcDNA5FRT vector using Lipofectamine 2000 (Life Technologies) according to the manufacturer's protocol. Twenty-four hours after transfection, CHO cells are split into F12 media containing 10% FBS, 2 mM L-Glutamine and 600-700 µg/ml hygromycin B (Sigma-Aldrich, St. Louis, MO) to select for transfected cells. 293 cells are split into DMEM media containing 10% FBS, 2 mM L-glutamine and 200 µg/ml hygromycin B. Expression of Notch receptors can be confirmed by FACS analysis using anti-human Notch1 PE (BioLegend, San Diego, CA), anti-Notch2 PE (eBioscience, San Diego, CA), or anti-human Notch3 PE (BioLegend, San Diego, CA).

To determine the specificity of binding to cell surface Notch proteins, the 28042 antibody is tested for binding to human Notch1, human Notch2, human Notch3 and murine Notch3 expressed on the surface of CHO cells by FACS analysis. Full length Notch receptor cDNAs cloned into pcDNA5FRT were transfected into FlpIn™ CHO cells and selected with 600 µg/ml hygromycin (Sigma), according to the manufacturer's protocol. Cell surface expression of Notch receptors is confirmed by FACS analysis using anti-Notch1 PE, anti-Notch2 PE or anti-Notch3 PE control antibodies (Biolegend). FlpIn™ CHO cells expressing Notch receptors are incubated with 5 µg/ml 28042 antibody or human IgG control antibody (Jackson ImmunoResearch) for 1 hour on ice, followed by washing with PBS/0.5% BSA, and incubation with anti-human PE secondary antibody (Biolegend) for 30 minutes on ice. FACS is performed on a BD FACSCanto II cell analyzer (BD Biosciences) and analyzed using FlowJo software.

Figure 7:
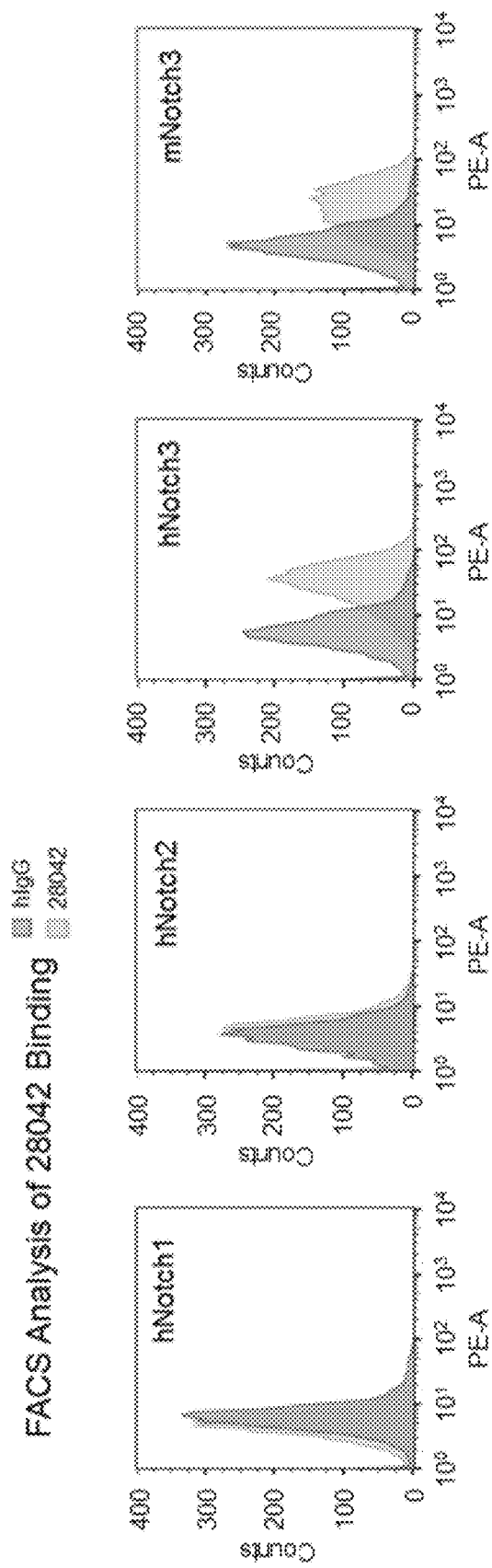
FIG. 7 shows the binding of the 28042 antibody to cell surface human Notch1, human Notch2, human Notch3, and murine Notch3 as observed by FACS. The results demonstrate that the 28042 antibody binds human and murine Notch3 while there is no appreciable binding of the 28042 antibody to Notch1 or Notch2.

As shown in FIG. 7, FACS binding data demonstrates that the 28042 antibody specifically binds to human Notch3 and murine Notch3, with no cross reactivity with human Notch1 or human Notch2.

To determine the specificity of binding to cell surface Notch proteins, the 28042 antibody is tested for binding to human Notch1, human Notch2, human Notch3 and murine Notch3 expressed on the surface of CHO cells using electrochemiluminescence (Meso Scale Discovery). A CHO line lacking any human Notch protein is used as a negative control. Cells are grown under standard conditions (37° C., F12+10% FBS). For binding studies, cells are washed in PBS containing calcium and magnesium, and removed from the plate by treatment with Cell Dissociation Buffer (Life Technologies) for ten minutes at 37° C.

Cells are seeded at a density of 30,000 cells per well, in hybridoma media, in a standard 96-well binding plates (Meso Scale Discovery, Cat. No. L15XA-6). Cells are incubated for one hour at 37° C. Antibodies or control IgG are added at 5 µg/mL, in 50 µL hybridoma media, and incubated for one hour at 37° C. The plates are washed twice with PBS containing 3% BSA. Binding of the antibodies to cell surface is detected using 2 µg/mL of MSD anti-mouse IgG secondary antibody (Meso Scale Discovery, Cat. No. R32AC-1) for one hour at 4° C. Plates are washed twice with PBS containing 3% BSA, and 150 µL of read buffer (Meso Scale Discovery Cat. No. R92TC-1) is added. The plates are analyzed on a Sector Imager 2400 instrument (Meso Scale Discovery).

Examples 4: Inhibition of Notch3-Ligand Binding

The 28042 antibody can be tested for its ability to inhibit the binding of rhNotch3 binding to human Jag1, Jag2, DLL1 and DLL4. Binding measurements are made by bio-layer interferometry (BLI), using a FortéBio Octet® QK instrument (FortéBio, Menlo Park, CA). The ligands tested are rhJag1-Fc (R&D Cat. No. 1277-JG-050), rhJag2-Fc (R&D Cat. No. 1726-JG-050), rhDLL1-Fc (R&D Cat. No. 5026-DL-050), and His tagged rhDLL4 (R&D Cat. No. 1506-D4-050).

To determine the degree of inhibition of Notch3-ligand binding by the 28042 antibody, the Octet sensors are loaded with recombinant human Notch3, and the antibody is allowed to bind. Then sensors are immersed in 500 µg/mL human IgG to block non-specific binding. Ligands are prepared at a concentration of 400 nM in PBS containing 3% BSA, and are allowed to bind. The on-rate and off-rate for ligand binding are detected using the Octet QK instrument and software.

Example 5: Inhibition of Ligand-Induced Notch3 ICD Cleavage

Activation of Notch receptors by ligands results in cleavage of the Notch intracellular domain (NICD), which can be detected by Western blot. In this example, the 28042 antibody is tested for its ability to inhibit ligand-induced cleavage of the Notch3 ICD.

To create soluble Notch ligands, PCR is used to amplify sequences corresponding to the extracellular domains of human Jag1 or human Jag2 cDNA and fuse them in-frame to the coding sequence of human or murine IgG Fc. This construct then is subcloned into the pEE14.4 expression vector (Lonza), transfected into CHOK1SV cells, and selected to produce stable cell lines that secrete hJag1-hFc, hJag1-mFc, hJag2-hFc, or hJag2-mFc fusion protein. Fusion proteins are purified from cell supernatants.

In one experiment, mNotch3 expressing cells are incubated with the Notch3 ligand Jag1, and ligand-induced cleavage of the mNotch3 ICD is measured by Western blot. The 28042 antibody is further added to test for its ability to inhibit ligand-induced cleavage of the mNotch3 ICD. 96-well Immunosorp ELISA plates (Nalgene Nunc, Rochester, NY) are coated with 5 µg/ml anti-mouse Fc (Jackson ImmunoResearch, West Grove, PA) overnight at 4° C. After washing wells with PBS/0.5% BSA, 5 µg/ml of soluble hJag1-mFc fusion protein is added and allowed to bind at room temperature for two hours. Unbound protein is removed by washing with PBS/0.5% BSA. 293 FlpIn™ cells engineered to express mNotch3 (produced as described in Example 3) are plated on captured ligand or mFc in the presence of 10 µg/mL human IgG control, the 28042 antibody, the Notch 3 antibody ABX, or an antibody specific for human Notch 3 (04F11) Cells are lysed 24 hours later in RIPA buffer (Boston BioProducts, Ashland, MA) containing protease inhibitors. Lysates are run on SDS PAGE, and transferred to nitrocellulose. Induction of NICD cleavage can be detected by probing with an antibody against the Notch3 C-terminus (Cell Signaling, Danvers, MA) that detects both full length protein and the cleaved ICD.

Figure 8:
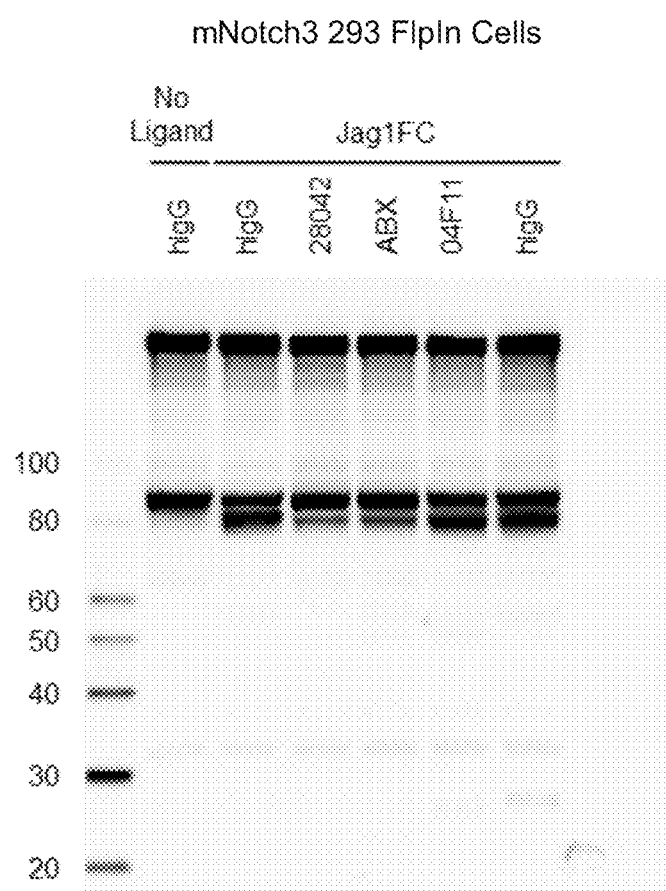
FIG. 8 is a Western blot that shows the level of inhibition of Jag1-induced Notch3 activation by the 28042 antibody as compared to other antibodies, as assessed by extent of intracellular domain cleavage of mNotch3 expressed in FlpIn™ cells.

As shown in FIG. 8, plating mNotch3 293 FlpIn™ cells on Jag1-mFc ligand induces ICD cleavage and activation of the receptor. Addition of the 28042 antibody diminishes ligand-induced cleavage and activation of mNotch3, while the addition of a human IgG control or a human Notch3 control antibody has no effect on mNotch3 ICD cleavage.

In another experiment, Notch3 expressing cells are incubated with the Notch3 ligand DLL4, and ligand-induced cleavage of the Notch3 ICD is measured by Western blot. The 28042 antibody is further added to test for its ability to inhibit ligand-induced cleavage of the Notch3 ICD. 96-well Immunosorp ELISA plates are coated with 5 µg/mL His tag antibody (R&D Systems, Minneapolis, MN) overnight at 4° C., after which 5 µg/mL DLL4-His fusion protein (R&D Systems, Minneapolis, MN), is added and allowed to bind for two hours at room temperature. Unbound protein is removed by washing with PBS/0.5% BSA. NCI-H838 cells are plated on captured ligand in the presence of 10 µg/mL human IgG control, the 28042 antibody, the Notch 3 antibody ABX, or an antibody specific for human Notch 3 (04F11). Cells are lysed 24 hours later in RIPA buffer (Boston BioProducts, Ashland, MA) containing protease inhibitors. Lysates are run on SDS PAGE, and transferred to nitrocellulose. Induction of NICD cleavage can be detected by probing with an antibody against the Notch3 C-terminus (Cell Signaling, Danvers, MA) that detects both full length protein and the cleaved ICD.

Figure 9:
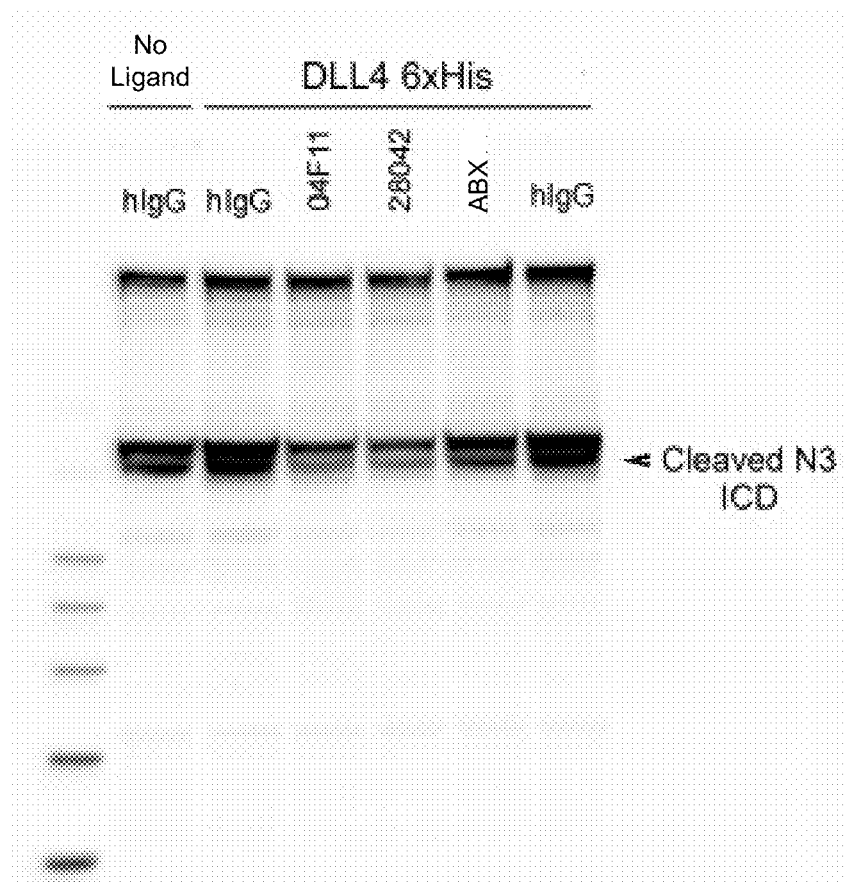
FIG. 9 is a Western blot that shows the level of inhibition of DLL4-induced human Notch3 receptor activation, as assessed by Notch3 intracellular domain cleavage in NCI-H838 cells plated on ligand in the presence of the 28042 antibody and other antibodies.

NCI-H838 cells exhibit low levels of constitutive human Notch3 activation as evidenced by the presence of cleaved N3 ICD even in absence of exogenous ligand, as shown in the Western blot in FIG. 9. As shown in FIG. 9, the 28042 antibody blocks further cleavage and activation of the Notch3 receptor in response to DLL4 stimulation and reduces the level of cleaved Notch3 ICD to below baseline levels, while a human IgG control antibody had no effect on Notch3 cleavage and activation.

In another experiment, murine or human Notch3 expressing cells are incubated with the Notch3 ligands Jag1, Jag2, and DLL4, and ligand-induced cleavage of the Notch3 ICD is measured by Western blot. The 28042 antibody is further added to test for its ability to inhibit ligand-induced cleavage of the Notch3 ICD. 96-well Maxisorp plates (Nunc) are coated overnight with 5 µg/ml anti-His tag (R&D Systems) or anti-mFc (Jackson ImmunoResearch) antibodies. After washing, 5 µg/ml recombinant DLL4 (R&D Systems, Minneapolis, MN), hJag1-mFc, or hJag2-mFc in PBS/0.5% BSA are added and allowed to bind for two hours at room temperature. No ligand control wells are coated with anti-mFc antibody overnight and incubated with 5 µg/ml mFc (Jackson ImmunoResearch). FlpIn™ CHO cells stably expressing human Notch3 or murine Notch3 are pre-incubated with 10 µg/ml of the 28042 antibody or hIgG control antibody for 30 minutes before plating 30,000 cells per well onto ligand-coated plates and incubating at 37° C. overnight. Cells are lysed 24 hours later in RIPA buffer (Boston BioProducts, Ashland, MA) containing protease inhibitors. Lysates are run on SDS PAGE, and transferred to nitrocellulose. Induction of NICD cleavage can be detected by probing with an antibody against the Notch3 C-terminus (Cell Signaling, Danvers, MA) that detects both full length protein and the cleaved ICD. An antibody against GAPDH (Cell Signaling) is used as a loading control. Bands are detected using an Odyssey CLx imaging system and Image Studio software (LI-COR).

Figure 10A:
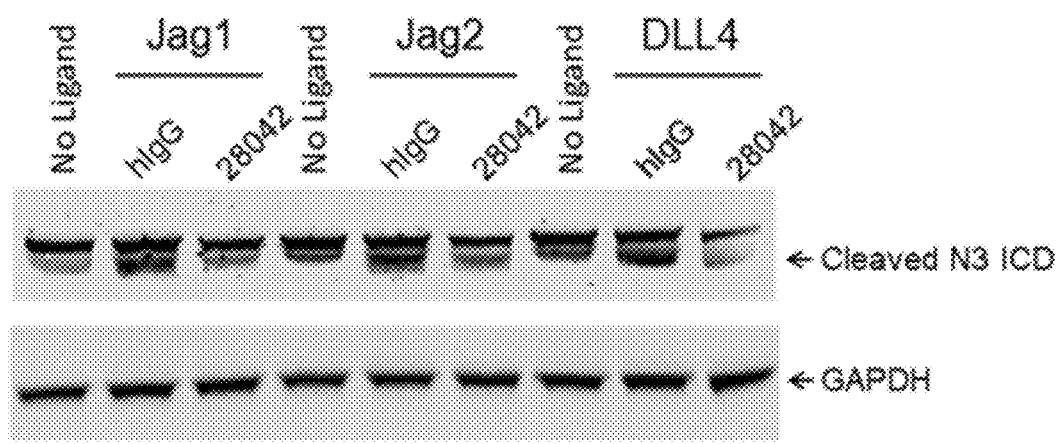
FIGS. 10A-B show the inhibition of ligand-induced Notch3 receptor activation, as assayed by Notch3 intracellular domain cleavage.
Figure 10B:
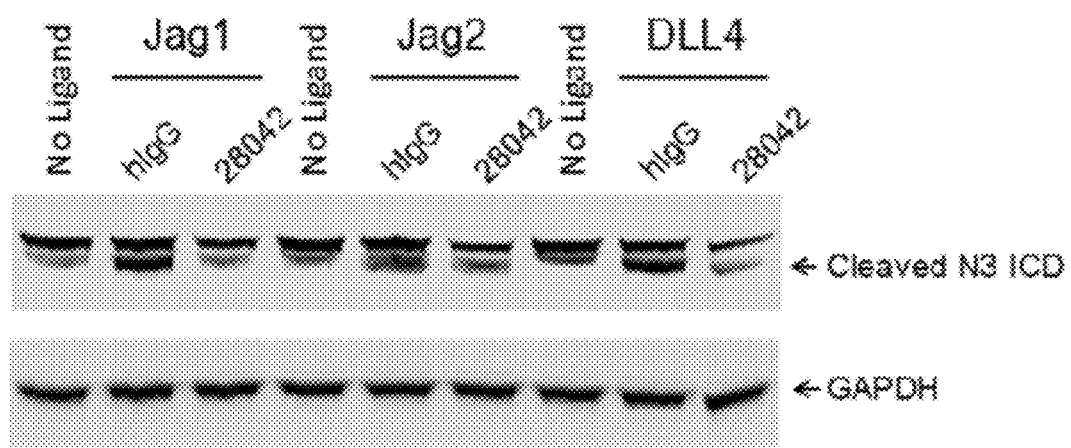

As shown in FIG. 10, in mouse (FIG. 10A) and human (FIG. 10B) Notch3-expressing cells, the 28042 antibody blocks Jag1, Jag2 or DLL4 ligand-induced cleavage and activation of Notch3.

Collectively, these results demonstrate the ability of the 28042 antibody to inhibit ligand-induced activation of Notch3.

Example 6: Inhibition of Notch3-Dependent Transcription

In this example, the 28042 antibody is tested for its ability to inhibit the transcription of Notch3 target genes. Reporter cells are generated that expressed luciferase in response to Notch3 activation, and the resulting luminescence is measured in the presence or absence of the 28042 antibody.

Reporter cell lines dependent upon Notch3 are produced via the lentiviral introduction of a RBP-Jκ-dependent luciferase reporter gene (SABiosciences, Frederick, MD) into 293-FlpIn Notch3 cells, RL95-2 endometrial cancer cells, HCC1143 breast cancer cells, and MDA-MB-468 breast cancer cells. To activate Notch3-dependent signaling and transcription, cells are plated on ligand-coated wells prepared as described in Example 5. Cells are pre-incubated with a 3-fold dilution series of Notch3 antibodies at concentrations ranging from 0-300 µg/mL, for one hour at 37° C., before seeding 100 µl of the suspension into 96-well plates coated with ligand or hFc. Cells are incubated in ligand-coated or murine-Fc-coated wells for four or twenty-four hours at 37° C., in 5% $CO_2$. Then, 100 µL of Promega Bright Glo™ (Promega, Madison, WI) is added to each well. The reaction is allowed to proceed for five minutes in the dark, and then the entire 200 µL volume is transferred into plates for analysis in a luminometer. Polyclonal antibodies directed against Notch1 (AF1057, R&D Systems), Notch2 (AF1190, R&D Systems) or Notch3 (AF1559, R&D Systems) are used as controls to confirm that ligand-stimulated reporter activity in each cell line is specifically dependent upon the introduced Notch receptor.

Figure 11:
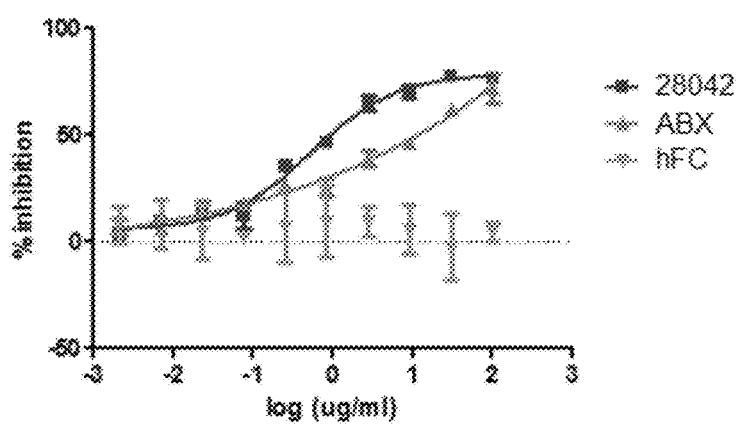
FIG. 11 is a dose-response curve based on a human Notch3 reporter assay showing that the 28042 antibody inhibits functional Notch3 activation, as measured by Notch3-dependent reporter gene expression in the presence of the Fc-bound ligand Jag2 (Jag2-Fc). The graph shows the inhibition of Jag2-Fc-stimulated reporter activity (% Inhibition) by antibody the 28042 antibody in stably transduced cells as a function of the amount of the 28042 antibody.

Data for a Notch3 Luciferase reporter assay for antibody 28042 is shown in FIG. 11. In this assay, cells of a MDA-MB-468 reporter cell line expressing endogenous human Notch3 and a RBP-Jκ luciferase reporter construct are plated on hJag2-mFc in the presence of Notch3 inhibitory antibodies. As shown therein, the 28042 antibody strongly inhibits the luminescent signal that results from Notch3 dependent transcription. The results demonstrate that the 28042 antibody inhibits Notch3-dependent transcription stimulated by the Jag2 ligand.

Example 7: Inhibition of Tumor Growth

In this example, the 28042 antibody is tested for its ability to inhibit tumor growth in vivo in a genetically engineered Notch3-driven tumor model that overexpresses and is dependent on mNotch3 for tumor maintenance. Approximately eleven week old NCR nude mice (Taconic, Germantown, NY) are inoculated subcutaneously into the right flank with $2\times10^5$ cells in 1:1 HBSS+Matrigel (Invitrogen, Carlsbad, CA)/Matrigel (BD Biosciences, San Jose, CA). Tumor measurements are taken twice weekly, using vernier calipers. Tumor volume is calculated using the formula: V=0.5× width×width×length. When tumors approach a volume of 150-200 mm³, mice are randomized into three groups of ten animals each. The next day, mice are treated with 20 mg/kg hIgG (control) or 20 mg/kg of the 28042 antibody or the ABX antibody by intraperitoneal injection. Mice are dosed twice weekly for the duration of the study. Forty-eight hours after final dosing, tumor volumes are measured again to assess tumor growth inhibition. All statistical analysis is done using GraphPad PRISM® Version 4.00. Final tumor volumes are analyzed using a one-way analysis of variance and Tukey multiple comparison test.

Figure 12A:
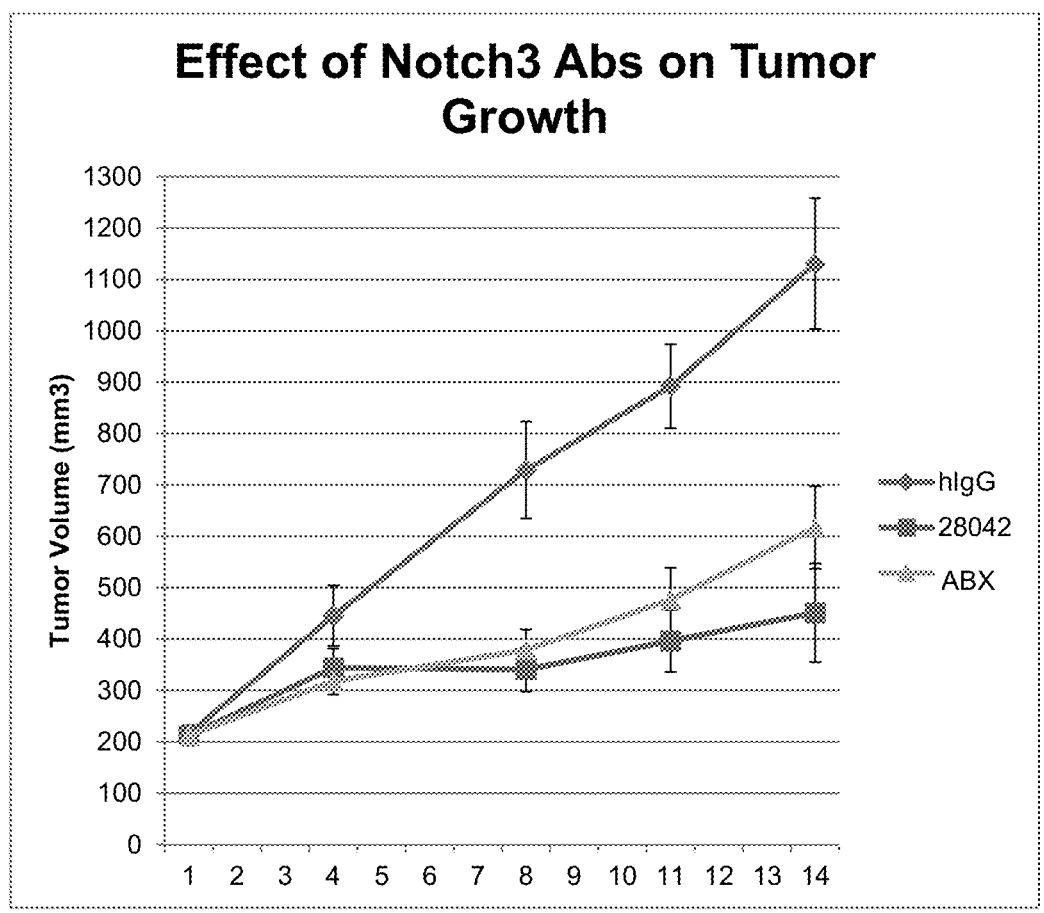
FIGS. 12A-B show the inhibition of tumor growth by the 28042 antibody in a Notch3-mediated mouse tumor model.

As shown in FIG. 12A, the treatment group (i.e., animals receiving the 28042 antibody) shows significant tumor growth inhibition, as compared to hIgG treated controls. All treatments are well-tolerated with no significant body weight loss.

Figure 12B:
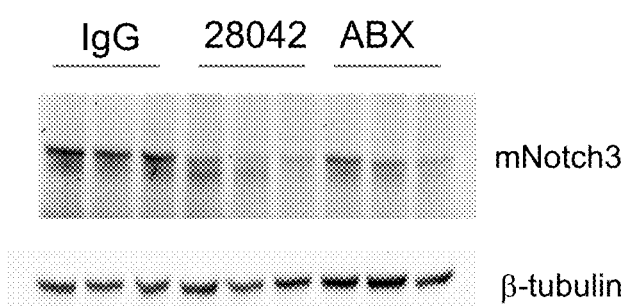

As shown in FIG. 12B, lysates from harvested tumor cells treated with the 28042 antibody showed a significant decrease in human Notch3 ICD cleavage over those treated with the control antibody, showing that the 28042 antibody reduces Notch3 activation in tumor cells.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

SEQUENCE LISTING

```
<160> NUMBER OF SEQ ID NOS: 42

<210> SEQ ID NO 1
<211> LENGTH: 451
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Met Met Ser Trp Val Arg Gln Ala Pro Gly Lys Gly Leu Glu Trp Val
        35                  40                  45

Ser Trp Ile Arg Ser Ser Gly Gly Thr Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Val Gly Gly Gly Thr Thr Gly Tyr Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

-continued

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Val Ser Gly
    50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

-continued

```
Thr Phe Gly Pro Gly Thr Lys Val Asp Phe Glu Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 3
<211> LENGTH: 5
<212> TYPE: PRT
<213> ORGANISM: Homo sapiens

<400> SEQUENCE: 3

```
Asp Tyr Met Met Ser
1               5
```

<210> SEQ ID NO 4
<211> LENGTH: 17
<212> TYPE: PRT
<213> ORGANISM: Homo sapiens

<400> SEQUENCE: 4

```
Trp Ile Arg Ser Ser Gly Gly Thr Thr Leu Tyr Ala Asp Ser Val Lys
1               5                   10                  15
Gly
```

<210> SEQ ID NO 5
<211> LENGTH: 12
<212> TYPE: PRT
<213> ORGANISM: Homo sapiens

<400> SEQUENCE: 5

```
Val Gly Gly Gly Thr Thr Gly Tyr Ala Phe Asp Ile
1               5                   10
```

<210> SEQ ID NO 6
<211> LENGTH: 121
<212> TYPE: PRT
<213> ORGANISM: Homo sapiens

<400> SEQUENCE: 6

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Met Met Ser Trp Val Arg Gln Ala Pro Gly Lys Gly Leu Glu Trp Val
        35                  40                  45
Ser Trp Ile Arg Ser Ser Gly Gly Thr Thr Leu Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Val Gly Gly Thr Thr Gly Tyr Ala Phe Asp Ile Trp Gly
            100                 105                 110

Gln Gly Thr Met Val Thr Val Ser Ser
        115                 120

<210> SEQ ID NO 7
<211> LENGTH: 11
<212> TYPE: PRT
<213> ORGANISM: Homo sapiens

<400> SEQUENCE: 7

Arg Ala Ser Gln Ser Ile Ser Asn Tyr Leu Asn
  1               5                  10

<210> SEQ ID NO 8
<211> LENGTH: 7
<212> TYPE: PRT
<213> ORGANISM: Homo sapiens

<400> SEQUENCE: 8

Gly Ala Ser Ser Leu Gln Ser
  1               5

<210> SEQ ID NO 9
<211> LENGTH: 9
<212> TYPE: PRT
<213> ORGANISM: Homo sapiens

<400> SEQUENCE: 9

Gln Gln Ser Tyr Ser Pro Ser Phe Thr
  1               5

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
             20                  25                  30

Leu Asn Trp Tyr Gln Gln Lys Pro Gly Lys Ala Pro Lys Leu Leu Ile
         35                  40                  45

Tyr Gly Ala Ser Ser Leu Gln Ser Gly Val Pro Ser Arg Val Ser Gly
     50                  55                  60

Thr Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Ser Phe
                 85                  90                  95

Thr Phe Gly Pro Gly Thr Lys Val Asp Phe Glu
            100                 105

<210> SEQ ID NO 11
<211> LENGTH: 1353
<212> TYPE: DNA
```

<213> ORGANISM: Homo sapiens

<400> SEQUENCE: 11

```
gaagttcaat tgttagagtc tggtggcggt cttgttcagc ctggtggttc tttacgtctt    60
tcttgcgctg cttccggatt cactttctct gattacatga tgtcttgggt tcgccaagct   120
cctggtaaag gtttggagtg gtttcttgg atccgttctt ctggtggcac tactctttat    180
gctgactccg ttaaaggtcg cttcactatc tctagagaca actctaagaa tactctctac   240
ttgcagatga acagcttaag ggctgaggac acagccacat attactgtgc gagagtcggt   300
ggtgggacca cgggttatgc ttttgatatc tggggccaag gacaatggt caccgtctca    360
agcgcctcaa caaaaggacc aagtgtgttc ccactcgccc ctagcagcaa gagtacatcc   420
ggggcactg cagcactcgg ctgcctcgtc aaggattatt ttccagagcc agtaaccgtg    480
agctggaaca gtggagcact cacttctggt gtccatactt ttcctgctgt cctgcaaagc   540
tctggcctgt actcactcag ctccgtcgtg accgtgccat cttcatctct gggcactcag   600
acctacatct gtaatgtaaa ccacaagcct agcaatacta aggtcgataa gcgggtggaa   660
cccaagagct gcgacaagac tcacacttgt cccccatgcc ctgcccctga acttctgggc   720
ggtcccagcg tctttttgtt cccacccaaa cctaaagata tctctgatga agtagaaca   780
cccgaggtga catgtgttgt tgtagacgtt tcccacgagg acccagaggt taagttcaac   840
tggtacgttg atggagtcga agtacataat gctaagacca gcctagaga ggagcagtat    900
aatagtacat accgtgtagt cagtgttctc acagtgctgc accaagactg gctcaacggc   960
aaagaataca aatgcaaagt gtccaacaaa gcactcccag cccctatcga aagactatt   1020
agtaaggcaa aggggcagcc tcgtgaacca caggtgtaca ctctgccacc cagtagagag  1080
gaaatgacaa agaaccaagt ctcattgacc tgcctggtga aaggcttcta ccccagcgac  1140
atcgccgttg agtgggagag taacggtcag cctgagaaca attacaagac aaccccccca  1200
gtgctggata tgacgggtc tttctttctg tacagtaagc tgactgtgga caagtcccgc   1260
tggcagcagg gtaacgtctt cagctgttcc gtgatgcacg aggcattgca caaccactac  1320
acccagaagt cactgagcct gagcccaggg aag                                1353
```

<210> SEQ ID NO 12
<211> LENGTH: 642
<212> TYPE: DNA
<213> ORGANISM: Homo sapiens

<400> SEQUENCE: 12

```
gacatccaga tgacccagtc tccatcctcc ctgtctgcat ctgtaggaga cagagtcacc    60
atcacttgcc gggcaagtca gagcattagc aactatttaa attggtatca gcagaaacca   120
gggaaagccc ctaagctcct gatctatggt gcatccagtt tgcaaagtgg ggtcccatca   180
agggtcagtg gcactggatc tgggacagat ttcactctta ccatcagcag tctgcaacct   240
gaagattttg caacttacta ctgtcaacag agttacagtc cctcattcac tttcggccct   300
gggaccaaag tggatttcga acgaactgtg gctgcaccat ctgtgttcat ctttccacca   360
agtgatgagc aactgaagtc tggtactgct tcagtcgtgt gtctgctgaa caatttctac   420
cctcgagaag ccaaagtcca atggaaggta gacaacgcac tgcagtccgg caatagccaa   480
gaatcagtta ccgaacagga ttcaaaggac agtacatatt ccctgagcag cactctgacc   540
ctgtcaaagg ccgattacga gaaacacaag gtctatgctt gcgaagtgac acatcaggga   600
ctgtccagcc cagtgacaaa atcttttaac cgtggggagt gt                       642
```

<210> SEQ ID NO 13
<211> LENGTH: 330
<212> TYPE: PRT
<213> ORGANISM: Homo sapiens

<400> SEQUENCE: 13

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 14
<211> LENGTH: 107
<212> TYPE: PRT
<213> ORGANISM: Homo sapiens

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15
<211> LENGTH: 321
<212> TYPE: DNA
<213> ORGANISM: Homo sapiens

<400> SEQUENCE: 15
cgaactgtgg ctgcaccatc tgtgttcatc tttccaccaa gtgatgagca actgaagtct      60
ggtactgctt cagtcgtgtg tctgctgaac aatttctacc ctcgagaagc aaagtccaa     120
tggaaggtag acaacgcact gcagtccggc aatagccaag aatcagttac cgaacaggat     180
tcaaaggaca gtacatattc cctgagcagc actctgaccc tgtcaaaggc cgattacgag     240
aaacacaagg tctatgcttg cgaagtgaca catcagggac tgtccagccc agtgacaaaa     300
tcttttaacc gtggggagtg t                                              321

<210> SEQ ID NO 16
<211> LENGTH: 990
<212> TYPE: DNA
<213> ORGANISM: Homo sapiens

<400> SEQUENCE: 16
gcctcaacaa aaggaccaag tgtgttccca ctcgccccta gcagcaagag tacatccggg      60
ggcactgcag cactcggctg cctcgtcaag gattattttc cagagccagt aaccgtgagc     120
tggaacagtg gagcactcac ttctggtgtc catactttte ctgctgtcct gcaaagctct     180
ggcctgtact cactcagctc cgtcgtgacc gtgccatctt catctctggg cactcagacc     240
tacatctgta atgtaaacca caagcctagc aatactaagg tcgataagcg ggtggaaccc     300
aagagctgcg acaagactca cacttgtccc ccatgccctg cccctgaact tctgggcggt     360
cccagcgtct ttttgttccc accaaagcct aaagatactc tgatgataag tagaacaccc     420
gaggtgacat gtgttgttgt agacgtttcc cacgaggacc cagaggttaa gttcaactgg     480
tacgttgatg gagtcgaagt acataatgct aagaccaagc ctagagagga gcagtataat     540
agtacatacc gtgtagtcag tgttctcaca gtgctgcacc aagactggct caacggcaaa     600
gaatacaaat gcaaagtgtc caacaaagca ctcccagccc ctatcgagaa gactattagt     660
aaggcaaagg ggcagcctcg tgaaccacag gtgtacactc tgccacccag tagagaggaa     720
atgacaaaga accaagtctc attgacctgc ctggtgaaag cttctaccc cagcgacatc     780
gccgttgagt gggagagtaa cggtcagcct gagaacaatt acaagacaac cccccagtg     840
ctggatagtg acgggtcttt ctttctgtac agtaagctga ctgtggacaa gtcccgctgg     900

```
cagcagggta acgtcttcag ctgttccgtg atgcacgagg cattgcacaa ccactacacc    960
cagaagtcac tgagcctgag cccagggaag                                    990

<210> SEQ ID NO 17
<211> LENGTH: 363
<212> TYPE: DNA
<213> ORGANISM: Homo sapiens

<400> SEQUENCE: 17
gaagttcaat tgttagagtc tggtggcggt cttgttcagc ctggtggttc tttacgtctt     60
tcttgcgctg cttccggatt cactttctct gattacatga tgtcttgggt tcgccaagct    120
cctggtaaag gtttggagtg ggtttcttgg atccgttctt ctggtggcac tactctttat    180
gctgactccg ttaaaggtcg cttcactatc tctagagaca actctaagaa tactctctac    240
ttgcagatga acagcttaag ggctgaggac acagccacat attactgtgc gagagtcggt    300
ggtgggacca cgggttatgc ttttgatatc tggggccaag gacaatggtc accgtctca     360 agc                                                                  363

<210> SEQ ID NO 18
<211> LENGTH: 321
<212> TYPE: DNA
<213> ORGANISM: Homo sapiens

<400> SEQUENCE: 18
gacatccaga tgacctagtc tccatcctcc ctgtctgcat ctgtaggaga cagagtcacc     60
atcacttgcc gggcaagtca gagcattagc aactatttaa attggtatca gcagaaacca    120
gggaaagccc ctaagctcct gatctatggt gcatccagtc tgcaaagtgg gtcccatca     180 agggtcagtg gcactggatc tgggacagat ttcactctta ccatcagcag tctgcaacct    240
gaagattttg caacttacta ctgtcaacag agttacagtc cctcattcac tttcggccct    300
gggaccaaag tggatttcga a                                              321

<210> SEQ ID NO 19
<211> LENGTH: 1604
<212> TYPE: PRT
<213> ORGANISM: Homo sapiens

<400> SEQUENCE: 19

Ala Pro Pro Cys Leu Asp Gly Ser Pro Cys Ala Asn Gly Gly Arg Cys
1               5                   10                  15

Thr Gln Leu Pro Ser Arg Glu Ala Ala Cys Leu Cys Pro Pro Gly Trp
            20                  25                  30

Val Gly Glu Arg Cys Gln Leu Glu Asp Pro Cys His Ser Gly Pro Cys
        35                  40                  45

Ala Gly Arg Gly Val Cys Gln Ser Ser Val Ala Gly Thr Ala Arg
    50                  55                  60

Phe Ser Cys Arg Cys Pro Arg Gly Phe Arg Gly Pro Asp Cys Ser Leu
65                  70                  75                  80

Pro Asp Pro Cys Leu Ser Ser Pro Cys Ala His Gly Ala Arg Cys Ser
                85                  90                  95

Val Gly Pro Asp Gly Arg Phe Leu Cys Ser Cys Pro Pro Gly Tyr Gln
            100                 105                 110

Gly Arg Ser Cys Arg Ser Asp Val Asp Glu Cys Arg Val Gly Glu Pro
        115                 120                 125
```

```
Cys Arg His Gly Gly Thr Cys Leu Asn Thr Pro Gly Ser Phe Arg Cys
130                 135                 140

Gln Cys Pro Ala Gly Tyr Thr Gly Pro Leu Cys Glu Asn Pro Ala Val
145                 150                 155                 160

Pro Cys Ala Pro Ser Pro Cys Arg Asn Gly Gly Thr Cys Arg Gln Ser
                165                 170                 175

Gly Asp Leu Thr Tyr Asp Cys Ala Cys Leu Pro Gly Phe Glu Gly Gln
                180                 185                 190

Asn Cys Glu Val Asn Val Asp Asp Cys Pro Gly His Arg Cys Leu Asn
        195                 200                 205

Gly Gly Thr Cys Val Asp Gly Val Asn Thr Tyr Asn Cys Gln Cys Pro
210                 215                 220

Pro Glu Trp Thr Gly Gln Phe Cys Thr Glu Asp Val Asp Glu Cys Gln
225                 230                 235                 240

Leu Gln Pro Asn Ala Cys His Asn Gly Gly Thr Cys Phe Asn Thr Leu
                245                 250                 255

Gly Gly His Ser Cys Val Cys Val Asn Gly Trp Thr Gly Glu Ser Cys
                260                 265                 270

Ser Gln Asn Ile Asp Asp Cys Ala Thr Ala Val Cys Phe His Gly Ala
        275                 280                 285

Thr Cys His Asp Arg Val Ala Ser Phe Tyr Cys Ala Cys Pro Met Gly
290                 295                 300

Lys Thr Gly Leu Leu Cys His Leu Asp Asp Ala Cys Val Ser Asn Pro
305                 310                 315                 320

Cys His Glu Asp Ala Ile Cys Asp Thr Asn Pro Val Asn Gly Arg Ala
                325                 330                 335

Ile Cys Thr Cys Pro Pro Gly Phe Thr Gly Gly Ala Cys Asp Gln Asp
                340                 345                 350

Val Asp Glu Cys Ser Ile Gly Ala Asn Pro Cys Glu His Leu Gly Arg
        355                 360                 365

Cys Val Asn Thr Gln Gly Ser Phe Leu Cys Gln Cys Gly Arg Gly Tyr
370                 375                 380

Thr Gly Pro Arg Cys Glu Thr Asp Val Asn Glu Cys Leu Ser Gly Pro
385                 390                 395                 400

Cys Arg Asn Gln Ala Thr Cys Leu Asp Arg Ile Gly Gln Phe Thr Cys
                405                 410                 415

Ile Cys Met Ala Gly Phe Thr Gly Thr Tyr Cys Glu Val Asp Ile Asp
                420                 425                 430

Glu Cys Gln Ser Ser Pro Cys Val Asn Gly Gly Val Cys Lys Asp Arg
        435                 440                 445

Val Asn Gly Phe Ser Cys Thr Cys Pro Ser Gly Phe Ser Gly Ser Thr
450                 455                 460

Cys Gln Leu Asp Val Asp Glu Cys Ala Ser Thr Pro Cys Arg Asn Gly
465                 470                 475                 480

Ala Lys Cys Val Asp Gln Pro Asp Gly Tyr Glu Cys Arg Cys Ala Glu
                485                 490                 495

Gly Phe Glu Gly Thr Leu Cys Asp Arg Asn Val Asp Asp Cys Ser Pro
                500                 505                 510

Asp Pro Cys His His Gly Arg Cys Val Asp Gly Ile Ala Ser Phe Ser
        515                 520                 525

Cys Ala Cys Ala Pro Gly Tyr Thr Gly Thr Arg Cys Glu Ser Gln Val
530                 535                 540

Asp Glu Cys Arg Ser Gln Pro Cys Arg His Gly Gly Lys Cys Leu Asp
```

```
545                 550                 555                 560
Leu Val Asp Lys Tyr Leu Cys Arg Cys Pro Ser Gly Thr Thr Gly Val
                565                 570                 575

Asn Cys Glu Val Asn Ile Asp Asp Cys Ala Ser Asn Pro Cys Thr Phe
                580                 585                 590

Gly Val Cys Arg Asp Gly Ile Asn Arg Tyr Asp Cys Val Cys Gln Pro
                595                 600                 605

Gly Phe Thr Gly Pro Leu Cys Asn Val Glu Ile Asn Glu Cys Ala Ser
                610                 615                 620

Ser Pro Cys Gly Glu Gly Gly Ser Cys Val Asp Gly Glu Asn Gly Phe
625                 630                 635                 640

Arg Cys Leu Cys Pro Gly Ser Leu Pro Leu Cys Leu Pro Pro
                645                 650                 655

Ser His Pro Cys Ala His Glu Pro Cys Ser His Gly Ile Cys Tyr Asp
                660                 665                 670

Ala Pro Gly Gly Phe Arg Cys Val Cys Glu Pro Gly Trp Ser Gly Pro
                675                 680                 685

Arg Cys Ser Gln Ser Leu Ala Arg Asp Ala Cys Glu Ser Gln Pro Cys
                690                 695                 700

Arg Ala Gly Gly Thr Cys Ser Ser Asp Gly Met Gly Phe His Cys Thr
705                 710                 715                 720

Cys Pro Pro Gly Val Gln Gly Arg Gln Cys Glu Leu Leu Ser Pro Cys
                725                 730                 735

Thr Pro Asn Pro Cys Glu His Gly Gly Arg Cys Glu Ser Ala Pro Gly
                740                 745                 750

Gln Leu Pro Val Cys Ser Cys Pro Gln Gly Trp Gln Gly Pro Arg Cys
                755                 760                 765

Gln Gln Asp Val Asp Glu Cys Ala Gly Pro Ala Pro Cys Gly Pro His
                770                 775                 780

Gly Ile Cys Thr Asn Leu Ala Gly Ser Phe Ser Cys Thr Cys His Gly
785                 790                 795                 800

Gly Tyr Thr Gly Pro Ser Cys Asp Gln Asp Ile Asn Asp Cys Asp Pro
                805                 810                 815

Asn Pro Cys Leu Asn Gly Gly Ser Cys Gln Asp Gly Val Gly Ser Phe
                820                 825                 830

Ser Cys Ser Cys Leu Pro Gly Phe Ala Gly Pro Arg Cys Ala Arg Asp
835                 840                 845

Val Asp Glu Cys Leu Ser Asn Pro Cys Gly Pro Gly Thr Cys Thr Asp
850                 855                 860

His Val Ala Ser Phe Thr Cys Thr Cys Pro Pro Gly Tyr Gly Gly Phe
865                 870                 875                 880

His Cys Glu Gln Asp Leu Pro Asp Cys Ser Pro Ser Ser Cys Phe Asn
                885                 890                 895

Gly Gly Thr Cys Val Asp Gly Val Asn Ser Phe Ser Cys Leu Cys Arg
                900                 905                 910

Pro Gly Tyr Thr Gly Ala His Cys Gln His Glu Ala Asp Pro Cys Leu
                915                 920                 925

Ser Arg Pro Cys Leu His Gly Gly Val Cys Ser Ala Ala His Pro Gly
930                 935                 940

Phe Arg Cys Thr Cys Leu Glu Ser Phe Thr Gly Pro Gln Cys Gln Thr
945                 950                 955                 960

Leu Val Asp Trp Cys Ser Arg Gln Pro Cys Gln Asn Gly Gly Arg Cys
                965                 970                 975
```

-continued

```
Val Gln Thr Gly Ala Tyr Cys Leu Cys Pro Gly Trp Ser Gly Arg
        980                 985                 990

Leu Cys Asp Ile Arg Ser Leu Pro Cys Arg Glu Ala Ala  Ala Gln Ile
        995                 1000                1005

Gly Val Arg Leu Glu Gln Leu Cys Gln Ala Gly Gly  Gln Cys Val
    1010                1015                1020

Asp Glu Asp Ser Ser His Tyr Cys Val Cys Pro Glu Gly Arg Thr
    1025                1030                1035

Gly Ser His Cys Glu Gln Glu Val Asp Pro Cys Leu Ala Gln Pro
    1040                1045                1050

Cys Gln His Gly Gly Thr Cys Arg Gly Tyr Met Gly Gly Tyr Met
    1055                1060                1065

Cys Glu Cys Leu Pro Gly Tyr Asn Gly Asp Asn Cys Glu Asp Asp
    1070                1075                1080

Val Asp Glu Cys Ala Ser Gln Pro Cys Gln His Gly Gly Ser Cys
    1085                1090                1095

Ile Asp Leu Val Ala Arg Tyr Leu Cys Ser Cys Pro Pro Gly Thr
    1100                1105                1110

Leu Gly Val Leu Cys Glu Ile Asn Glu Asp Asp Cys Gly Pro Gly
    1115                1120                1125

Pro Pro Leu Asp Ser Gly Pro Arg Cys Leu His Asn Gly Thr Cys
    1130                1135                1140

Val Asp Leu Val Gly Gly Phe Arg Cys Thr Cys Pro Pro Gly Tyr
    1145                1150                1155

Thr Gly Leu Arg Cys Glu Ala Asp Ile Asn Glu Cys Arg Ser Gly
    1160                1165                1170

Ala Cys His Ala Ala His Thr Arg Asp Cys Leu Gln Asp Pro Gly
    1175                1180                1185

Gly Gly Phe Arg Cys Leu Cys His Ala Gly Phe Ser Gly Pro Arg
    1190                1195                1200

Cys Gln Thr Val Leu Ser Pro Cys Glu Ser Gln Pro Cys Gln His
    1205                1210                1215

Gly Gly Gln Cys Arg Pro Ser Pro Gly Pro Gly Gly Gly Leu Thr
    1220                1225                1230

Phe Thr Cys His Cys Ala Gln Pro Phe Trp Gly Pro Arg Cys Glu
    1235                1240                1245

Arg Val Ala Arg Ser Cys Arg Glu Leu Gln Cys Pro Val Gly Val
    1250                1255                1260

Pro Cys Gln Gln Thr Pro Arg Gly Pro Arg Cys Ala Cys Pro Pro
    1265                1270                1275

Gly Leu Ser Gly Pro Ser Cys Arg Ser Phe Pro Gly Ser Pro Pro
    1280                1285                1290

Gly Ala Ser Asn Ala Ser Cys Ala Ala Ala Pro Cys Leu His Gly
    1295                1300                1305

Gly Ser Cys Arg Pro Ala Pro Leu Ala Pro Phe Phe Arg Cys Ala
    1310                1315                1320

Cys Ala Gln Gly Trp Thr Gly Pro Arg Cys Glu Ala Pro Ala Ala
    1325                1330                1335

Ala Pro Glu Val Ser Glu Glu Pro Arg Cys Pro Arg Ala Ala Cys
    1340                1345                1350

Gln Ala Lys Arg Gly Asp Gln Arg Cys Asp Arg Glu Cys Asn Ser
    1355                1360                1365
```

```
Pro Gly Cys Gly Trp Asp Gly Gly Asp Cys Ser Leu Ser Val Gly
    1370            1375            1380

Asp Pro Trp Arg Gln Cys Glu Ala Leu Gln Cys Trp Arg Leu Phe
    1385            1390            1395

Asn Asn Ser Arg Cys Asp Pro Ala Cys Ser Ser Pro Ala Cys Leu
    1400            1405            1410

Tyr Asp Asn Phe Asp Cys His Ala Gly Gly Arg Glu Arg Thr Cys
    1415            1420            1425

Asn Pro Val Tyr Glu Lys Tyr Cys Ala Asp His Phe Ala Asp Gly
    1430            1435            1440

Arg Cys Asp Gln Gly Cys Asn Thr Glu Glu Cys Gly Trp Asp Gly
    1445            1450            1455

Leu Asp Cys Ala Ser Glu Val Pro Ala Leu Leu Ala Arg Gly Val
    1460            1465            1470

Leu Val Leu Thr Val Leu Leu Pro Pro Glu Glu Leu Leu Arg Ser
    1475            1480            1485

Ser Ala Asp Phe Leu Gln Arg Leu Ser Ala Ile Leu Arg Thr Ser
    1490            1495            1500

Leu Arg Phe Arg Leu Asp Ala His Gly Gln Ala Met Val Phe Pro
    1505            1510            1515

Tyr His Arg Pro Ser Pro Gly Ser Glu Pro Arg Ala Arg Arg Glu
    1520            1525            1530

Leu Ala Pro Glu Val Ile Gly Ser Val Val Met Leu Glu Ile Asp
    1535            1540            1545

Asn Arg Leu Cys Leu Gln Ser Pro Glu Asn Asp His Cys Phe Pro
    1550            1555            1560

Asp Ala Gln Ser Ala Ala Asp Tyr Leu Gly Ala Leu Ser Ala Val
    1565            1570            1575

Glu Arg Leu Asp Phe Pro Tyr Pro Leu Arg Asp Val Arg Gly Glu
    1580            1585            1590

Pro Leu Glu Pro Pro Glu Pro Ser Val Pro Leu
    1595            1600

<210> SEQ ID NO 20
<211> LENGTH: 428
<212> TYPE: PRT
<213> ORGANISM: Homo sapiens

<400> SEQUENCE: 20

Ala Pro Pro Cys Leu Asp Gly Ser Pro Cys Ala Asn Gly Gly Arg Cys
1               5                   10                  15

Thr Gln Leu Pro Ser Arg Glu Ala Ala Cys Leu Cys Pro Pro Gly Trp
                20                  25                  30

Val Gly Glu Arg Cys Gln Leu Glu Asp Pro Cys His Ser Gly Pro Cys
            35                  40                  45

Ala Gly Arg Gly Val Cys Gln Ser Ser Val Val Ala Gly Thr Ala Arg
        50                  55                  60

Phe Ser Cys Arg Cys Pro Arg Gly Phe Arg Gly Pro Asp Cys Ser Leu
65                  70                  75                  80

Pro Asp Pro Cys Leu Ser Ser Pro Cys Ala His Gly Ala Arg Cys Ser
                85                  90                  95

Val Gly Pro Asp Gly Arg Phe Leu Cys Ser Cys Pro Pro Gly Tyr Gln
            100                 105                 110

Gly Arg Ser Cys Arg Ser Asp Val Asp Glu Cys Arg Val Gly Glu Pro
        115                 120                 125
```

-continued

Cys Arg His Gly Gly Thr Cys Leu Asn Thr Pro Gly Ser Phe Arg Cys
130                 135                 140

Gln Cys Pro Ala Gly Tyr Thr Gly Pro Leu Cys Glu Asn Pro Ala Val
145                 150                 155                 160

Pro Cys Ala Pro Ser Pro Cys Arg Asn Gly Gly Thr Cys Arg Gln Ser
            165                 170                 175

Gly Asp Leu Thr Tyr Asp Cys Ala Cys Leu Pro Gly Phe Glu Gly Gln
            180                 185                 190

Asn Cys Glu Val Asn Val Asp Asp Cys Pro Gly His Arg Cys Leu Asn
        195                 200                 205

Gly Gly Thr Cys Val Asp Gly Val Asn Thr Tyr Asn Cys Gln Cys Pro
210                 215                 220

Pro Glu Trp Thr Gly Gln Phe Cys Thr Glu Asp Val Asp Glu Cys Gln
225                 230                 235                 240

Leu Gln Pro Asn Ala Cys His Asn Gly Gly Thr Cys Phe Asn Thr Leu
            245                 250                 255

Gly Gly His Ser Cys Val Cys Val Asn Gly Trp Thr Gly Glu Ser Cys
            260                 265                 270

Ser Gln Asn Ile Asp Asp Cys Ala Thr Ala Val Cys Phe His Gly Ala
            275                 280                 285

Thr Cys His Asp Arg Val Ala Ser Phe Tyr Cys Ala Cys Pro Met Gly
290                 295                 300

Lys Thr Gly Leu Leu Cys His Leu Asp Asp Ala Cys Val Ser Asn Pro
305                 310                 315                 320

Cys His Glu Asp Ala Ile Cys Asp Thr Asn Pro Val Asn Gly Arg Ala
            325                 330                 335

Ile Cys Thr Cys Pro Pro Gly Phe Thr Gly Gly Ala Cys Asp Gln Asp
            340                 345                 350

Val Asp Glu Cys Ser Ile Gly Ala Asn Pro Cys Glu His Leu Gly Arg
        355                 360                 365

Cys Val Asn Thr Gln Gly Ser Phe Leu Cys Gln Cys Gly Arg Gly Tyr
370                 375                 380

Thr Gly Pro Arg Cys Glu Thr Asp Val Asn Glu Cys Leu Ser Gly Pro
385                 390                 395                 400

Cys Arg Asn Gln Ala Thr Cys Leu Asp Arg Ile Gly Gln Phe Thr Cys
            405                 410                 415

Ile Cys Met Ala Gly Phe Thr Gly Thr Tyr Cys Glu
            420                 425

<210> SEQ ID NO 21
<211> LENGTH: 11
<212> TYPE: PRT
<213> ORGANISM: Homo sapiens

<400> SEQUENCE: 21

Arg Ala Ser Gln Ser Ile Ser Ser Tyr Leu Asn
1               5                   10

<210> SEQ ID NO 22
<211> LENGTH: 7
<212> TYPE: PRT
<213> ORGANISM: Homo sapiens

<400> SEQUENCE: 22

Ala Ala Ser Ser Leu Gln Ser
1               5

```
<210> SEQ ID NO 23
<211> LENGTH: 107
<212> TYPE: PRT
<213> ORGANISM: Homo sapiens

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Val Ser Gly
    50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu
            100                 105

<210> SEQ ID NO 24
<211> LENGTH: 107
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Val Ser Gly
    50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu
            100                 105

<210> SEQ ID NO 25
<211> LENGTH: 107
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Val Ser Gly
    50                  55                  60
```

```
Thr Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Ser Phe
                 85                  90                  95

Thr Phe Gly Pro Gly Thr Lys Val Asp Ile Glu
            100                 105

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
                 20                  25                  30

Leu Asn Trp Tyr Gln Gln Lys Pro Gly Lys Ala Pro Lys Leu Leu Ile
             35                  40                  45

Tyr Gly Ala Ser Ser Leu Gln Ser Gly Val Pro Ser Arg Val Ser Gly
 50                  55                  60

Thr Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Ser Phe
                 85                  90                  95

Thr Phe Gly Pro Gly Thr Lys Val Asp Phe Lys
            100                 105

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Val Ser Gly
 50                  55                  60

Thr Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Ser Phe
                 85                  90                  95

Thr Phe Gly Pro Gly Thr Lys Val Asp Phe Glu
            100                 105

<210> SEQ ID NO 28
<211> LENGTH: 107
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
```

```
            20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Val Ser Gly
        50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Ile Lys
                100                 105

<210> SEQ ID NO 29
<211> LENGTH: 107
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Val Ser Gly
        50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Ile Lys
                100                 105

<210> SEQ ID NO 30
<211> LENGTH: 214
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Val Ser Gly
        50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 214
<212> TYPE: PRT
<213> ORGANISM: Homo sapiens

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Val Ser Gly
    50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 214
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
```

```
            20                  25                  30
Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Val Ser Gly
        50                  55                  60

Thr Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Ile Glu Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 214
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Val Ser Gly
        50                  55                  60

Thr Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 214
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Val Ser Gly
    50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 214
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Val Ser Gly
    50                  55                  60

-continued

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 214
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Val Ser Gly
    50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 107
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu
            100                 105

<210> SEQ ID NO 38
<211> LENGTH: 107
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Val Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu
            100                 105

<210> SEQ ID NO 39
<211> LENGTH: 107
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Ser Phe
                 85                  90                  95

Thr Phe Gly Pro Gly Thr Lys Val Asp Phe Glu
            100                 105

<210> SEQ ID NO 40
<211> LENGTH: 214
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
                 20                  25                  30

Leu Asn Trp Tyr Gln Gln Lys Pro Gly Lys Ala Pro Lys Leu Leu Ile
             35                  40                  45

Tyr Gly Ala Ser Ser Leu Gln Ser Gly Val Pro Ser Arg Phe Ser Gly
 50                  55                  60

Thr Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Ser Phe
                 85                  90                  95

Thr Phe Gly Pro Gly Thr Lys Val Asp Phe Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 214
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
                 20                  25                  30

Leu Asn Trp Tyr Gln Gln Lys Pro Gly Lys Ala Pro Lys Leu Leu Ile
             35                  40                  45

Tyr Gly Ala Ser Ser Leu Gln Ser Gly Val Pro Ser Arg Val Ser Gly
 50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 42
<211> LENGTH: 214
<212> TYPE: PRT
<213> ORGANISM: Homo sapiens

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Ser Phe
                85                  90                  95

Thr Phe Gly Pro Gly Thr Lys Val Asp Phe Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210
```

What is claimed is:

1. A method of inhibiting or reducing ligand-induced Notch3 activity in a mammal, the method comprising exposing the mammal to an effective amount of an antibody that binds human Notch3, wherein the antibody comprises:
   (a) an immunoglobulin heavy chain variable region (VH) comprising a $CDR_{H1}$, $CDR_{H2}$, and $CDR_{H3}$, wherein the $CDR_{H1}$, $CDR_{H2}$, and $CDR_{H3}$ comprise the $CDR_{H1}$, $CDR_{H2}$, and $CDR_{H3}$ of a VH amino acid sequence set forth in SEQ ID NO: 6; and
   (b) an immunoglobulin light chain variable region (VL) comprising a $CDR_{L1}$, $CDR_{L2}$, and $CDR_{L3}$, wherein the $CDR_{L1}$, $CDR_{L2}$, and $CDR_{L3}$ comprise the $CDR_{L1}$, $CDR_{L2}$, and $CDR_{L3}$ of a VL amino acid sequence set forth in any one of SEQ ID NO: 10, 23, 24, 25, 26, 27, 28, 29, 37, 38, or 39.

2. The method of claim 1, wherein the mammal has a cancer selected from the group consisting of breast cancer, lung cancer, pancreatic cancer, endometrial cancer, ovarian cancer, prostate cancer, cervical cancer, brain cancer, skin cancer, colorectal cancer, gastric cancer, head and neck cancer, gastrointestinal cancer, sarcoma, and hematopoietic cell cancer.

3. The method of claim 2, wherein the brain cancer is glioblastoma, astrocytoma, or neuroblastoma.

4. The method of claim 2, wherein the sarcoma is rhabdomyosarcoma or osteosarcoma.

5. The method of claim 2, wherein the hematopoietic cell cancer is multiple myeloma or leukemia.

6. The method of claim 5, wherein the leukemia is T-ALL, B-ALL, or B-CLL.

7. The method of claim 1, wherein the mammal is a human.

8. The method of claim 1, wherein the amino acid sequence of the VH comprises a $CDR_{H1}$ comprising the amino acid sequence of SEQ ID NO: 3, a $CDR_{H2}$ comprising the amino acid sequence of SEQ ID NO: 4, and a $CDR_{H3}$ comprising the amino acid sequence of SEQ ID NO: 5, and wherein the amino acid sequence of the VL comprises a $CDR_{L1}$ comprising the amino acid sequence of SEQ ID NO: 7 or SEQ ID NO: 21, a $CDR_{L2}$ comprising the amino acid sequence of SEQ ID NO: 8 or SEQ ID NO: 22, and a $CDR_{L3}$ comprising the amino acid sequence of SEQ ID NO: 9.

9. The method of claim 1, wherein the amino acid sequence of the VH comprises the amino acid sequence of SEQ ID NO: 6, and wherein the amino acid sequence of the VL comprises the amino acid sequence of SEQ ID NO: 10, 23, 24, 25, 26, 27, 28, 29, 37, 38, or 39.

10. The method of claim 1, wherein the antibody comprises an immunoglobulin heavy chain comprising the amino acid sequence of SEQ ID NO: 1, and an immunoglobulin light chain comprising the amino acid sequence of SEQ ID NO: 2, 30, 31, 32, 33, 34, 35, 36, 40, 41, or 42.

11. The method of claim 1, wherein the ligand is selected from the group consisting of Jag1, Jag2, DLL1, and DLL2.

12. The method of claim 1, wherein the ligand-induced Notch3 activity is ligand-induced Notch3 intracellular domain (ICD) cleavage.

13. The method of claim 1, wherein the ligand-induced Notch3 activity is ligand-induced Notch3-mediated transcription.

* * * * *